(12) United States Patent
Wong et al.

(10) Patent No.: US 7,323,303 B2
(45) Date of Patent: Jan. 29, 2008

(54) MODIFIED β-LACTAMASES AND USES THEREOF

(75) Inventors: Kwok-Yin Wong, Hong Kong SAR (CN); Thomas Yun-Chung Leung, Hong Kong SAR (CN); Pak-Ho Chan, Hong Kong SAR (CN)

(73) Assignee: Hong Kong Polytechnic University, Hong Kong SAR (HK)

( * ) Notice: Subject to any disclaimer, the term of this patent is extended or adjusted under 35 U.S.C. 154(b) by 337 days.

(21) Appl. No.: 10/401,867

(22) Filed: Mar. 31, 2003

(65) Prior Publication Data

US 2005/0261270 A1   Nov. 24, 2005

(51) Int. Cl.
 C12Q 1/34 (2006.01)
 C12N 9/86 (2006.01)
 C12N 15/55 (2006.01)
 C12N 15/70 (2006.01)

(52) U.S. Cl. ............... 435/6; 435/231; 435/252.3; 435/320.1; 536/23.2

(58) Field of Classification Search ............ None
 See application file for complete search history.

(56) References Cited

U.S. PATENT DOCUMENTS

| | | | | |
|---|---|---|---|---|
| 4,910,141 A * | 3/1990 | Wong et al. | ............ | 536/23.1 |
| 5,472,855 A * | 12/1995 | Carter et al. | ............ | 435/68.1 |
| 5,508,192 A | 4/1996 | Georgiou et al. | | |
| 5,677,153 A * | 10/1997 | Botstein et al. | ............ | 435/91.4 |
| 5,741,657 A | 4/1998 | Tsien et al. | | |
| 5,824,469 A * | 10/1998 | Horwitz et al. | ............ | 435/6 |
| 6,391,640 B1 * | 5/2002 | Minshull et al. | ............ | 435/440 |
| 6,562,617 B1 * | 5/2003 | Anderson et al. | ............ | 435/325 |

FOREIGN PATENT DOCUMENTS

JP   2002-250730 A   6/2002

OTHER PUBLICATIONS

Escobar, W. A., et al., 1994, "Site-directed mutagenesis of glutamate-166 in β-lactamase leads to a branched path mechanism", Biochemistry, vol. 33, pp. 7619-7626.*
Raquet, X., et al., 1995, Stability of TEM β-lactamase mutatns hydrolyzing third generation cephalosporins, PROTEINS: Structure, Function, and Genetics, vol. 23, pp. 63-72.*
Machine-Assisted Translation of JP 2002-250730-A, Morii et al., published Sep. 6, 2003, "A molecule sensor and its manufacturing method", 17 pages as translated.*

(Continued)

Primary Examiner—Nashaat T. Nashed
Assistant Examiner—William W. Moore
(74) Attorney, Agent, or Firm—Buchanan Ingersoll & Rooney PC

(57) ABSTRACT

A tool that can screen bacteria for β-lactamases against a panel of various antibiotics is desirable. A biosensor incorporating an indicator molecule into β-lactamases may achieve this purpose, but it requires that the attached indicator molecule must not impair the binding affinity of the protein to a great extent to provide a higher sensitivity. A modified β-lactamases with a residue on the Ω-loop or outside the Ω-loop but close to the active site of β-lactamase being replaced by a reactive residue is developed in this invention.

3 Claims, 33 Drawing Sheets

OTHER PUBLICATIONS

Bouthers et al., "Role of residues 104, 164, 166, 238, and 240 in the Substrate Profile of PER-1 β-Lactamase Hydrolysing Third-Generation Cephalosporins", Biochem Journal (1998), vol. 330, pp. 1143-1149, Great Britain.

Mustafi et al., "Structure of Spin-Labeled Methylmethanethiolsulfonate in Solution and Bound to TEM-1 β-Lactamase Determined by Electron Nuclear Double Resonance Spectroscopy", Biochemistry, vol. 41, No. 3, pp. 741-808, 2002.

P.J. Madgwick et al., "β-lactamase I from *Bacillus cereus*, Structure and Site-directed Mutagenesis", Biochem. J., (1987), pp. 657-662, vol. 248.

R. Aschaffenburg et al., "Preliminary Crystallographic Data for β-lactamase I from *Bacillus cereus*", J. Mol. Biol., (1978), pp. 447-449, vol. 120.

B. Samraoui et al., "Tertiary Structural Similarity Between A Class A β-lactamase and a Penicillin-sensitive D-alanyl Carboxypeptidase-transpeptidase", Nature, Mar. 27, 1986, pp. 378-380, vol. 320.

Paul C. Moews et al., "β-lactamase of *Bacillus licheniformis* 749/C at 2 ÅResolution", Proteins 7, (1990), pp. 156-171.

Yun-Chung Leung et al., "Site-directed Mutagenesis of β-lactamase I: role of Glu-166", Biochem J. (1994), pp. 671-678, vol. 299.

Susan J. Thornewell et al."An Efficient Expression and Secretion System Based on *Bacillus subtilis* phage φ105 and Its Use for the Production of *B. cereus* β-lactamase I", Gene, (1993), pp. 47-53.

Chan, Pak-Ho. et al., "Biosensor for beta-lactam antibiotics based on fluorophore-labelled beta-lactamase mutant." Database Biosis, Biosciences Information Service, Philadelphia, PA, 2002 and Abstracts of Papers American Chemical Society, vol. 223, No. 1-2, 2002, p. 39, 223rd National Meeting of the American Chemical Society, Orlando, FL, Apr. 7-11, 2002.

Escobar, Walter et al., "Site-Directed Mutagenesis of Glutamate-166 in β-Lactamase Leads to a Branched Path Mechanism." Biochemistry, vol. 33, No. 24, 1994, pp. 7619-7626.

Gibson, R.M. et al., "Site-Directed Mutagenesis of β-Lactamase I Single and Double Mutants of Glu-166 and Lys-73." Biochemical Journal, vol. 272, No. 3, 1990, pp. 613-620.

Petrosino, Joseph F.et al., "Systematic Mutagenesis of the Active Site Omega Loop of TEM-1 β-Lactamase." Journal of Bacteriology, vol. 178, No. 7, Apr. 1996, pp. 1821-1828.

Marvin, Jonathan S. et al., "Engineering Biosensors by Introducting Fluorescent Allosteric Signal Transducers: Construction of a Novel Glucose Sensor." Journal of the American Chemical Society, American Chemical Society, Washington, D.C., vol. 120, No. 1, 1998, pp. 7-11.

Mustafi, D. et al., "Endor Structural Characterization of a Catalytically Competent Acylenzyme Reaction Intermediate of Wild-Type TEM-1 Beta-Lactamase Confirms Glutamate-166 as the Base Catalyst", Biochemistry, Jan. 27, 2001; 40(8):2397-409.

Vanwetswinkel, S. et al., "Selection of Beta-Lactamase and Penicillin Binding Mutants From a Library of Phage Displayed TEM-1 Beta-Lactamase Randomly Mutated in the Active Site Omega-Loop", J. Mol. Biol., Jan. 21, 2001; 295(3): 527-40.

Bouthors, AT et al., "Role of Residues 104, 164, 166, 238 and 240 in the Substrate Profile of PER-1 Beta-Lactamase Hydrolysing Third-Generation Cephalosporins", Biochem. J., Mar. 15, 1998; 330 (Pt. 3): 1443-9.

Leung, YC et al., "Site-Directed Mutagenesis of Beta-Lactamase I: Role of GLU-166", Biochem J., May 1, 1994; 299 (Pt. 3): 671-8.

Calciano, LJ et al., "Side-Chain Mobility of the Beta-Lactamase a State Probed by Electron Spin Resonance Spectroscopy", Biochemistry, Jun. 1, 1993; 32(21):55644-9.

Christensen, Henriette et al., "β-Lactamases as Fully Efficiant Enzymes", Biochem J. (1990) 266, 853-861.

* cited by examiner ized
MODIFIED β-LACTAMASES AND USES THEREOF

FIELD OF THE INVENTION

This invention relates to modified β-lactamases that can be used in the detection of β-lactam antibiotics and β-lactamase inhibitors, and/or in screening bacteria for β-lactamases against a panel of β-lactam antibiotics.

BACKGROUND OF THE INVENTION

β-Lactam antibiotics (e.g. penicillins and cephalosporins) are an important class of antibacterial agents widely used in clinical therapies and as health promoting agents in animal feedstuffs. The clinical function of β-lactam antibiotics relies on their inhibitory effect on the activity of penicillin-binding proteins which are responsible for synthesizing bacterial cell wall. However, the clinical importance of β-lactam antibiotics has been challenged by the emergence of β-lactamases which are capable of inactivating β-lactam antibiotics by hydrolyzing the β-lactam ring to carboxylic acid. To respond to this clinical problem, the pharmaceutical industry has produced a wide range of β-lactam antibiotics (which have stronger resistance toward the hydrolyzing action of β-lactamases) and new β-lactamase inhibitors (which can irreversibly block the enzyme's active site via covalent modification). In order to search for a potent antibiotic from a large pool of drug candidates rapidly, a convenient tool that can screen bacteria for β-lactamases against a panel of various antibiotics is desirable. Moreover, a sensing tool that can detect β-lactamase inhibitors and β-lactam antibiotics can also be useful. Such a tool can be used in the discovery of β-lactam antibiotics and new β-lactamase inhibitors, and utilized in routine measurement of antibiotic residues in liquid and food samples (e.g. milk).

OBJECTS OF THE INVENTION

Therefore, it is an object of this invention to resolve at least one or more of the problems as set forth in the prior art. As a minimum, it is an object of this invention to provide the public with a useful choice.

SUMMARY OF THE INVENTION

Accordingly, this invention provides β-lactamases with a non-reactive residue replaced by a reactive residue.

Preferably the reactive residue is selected from the group consisting of amino acids containing a free alcohol group, amino acids containing a free carboxylic acid group, or amino acids containing a free amine group. More preferably, the reactive residue is cysteine.

Preferably, the non-reactive residue is on the Ω-loop of said β-lactamase.

Preferably, the reactive residue is further reacted with an indicator molecule to generate a signal to detect β-lactam antibiotics or β-lactamase inhibitors. More preferably, the indicator molecule is a fluorophore.

Optionally, the non-reactive residue is Glu-166 residue.

Preferably, the β-lactamase is a mutant. More preferably, the β-lactamase is a singly mutated mutant. Alternatively, the β-lactamase is a multiply mutated mutant. For example, in one specific embodiment, the β-lactamase is a E166C mutant.

A second aspect of this invention provides a method for detecting β-lactam antibiotics or β-lactamase inhibitors in a sample, including the steps of:
  exposing the sample to a β-lactamase with a non-reactive residue on the Ω-loop replaced by a reactive residue, for binding said β-lactamase with said β-lactam antibiotics or β-lactamase inhibitors;
  detecting a signal emitted by the β-lactamase bound with said β-lactam antibiotics or β-lactamase inhibitors.

Preferably, the method of this invention further includes the step of comparing the signal emitted by the β-lactamase bound with said β-lactam antibiotics or β-lactamase inhibitors, with a signal emitted by the β-lactamase from a control sample having no β-lactam antibiotics and β-lactamase inhibitors.

Yet another aspect of this invention provides an apparatus for detecting β-lactam antibiotics or β-lactamase inhibitors in a sample incorporating a β-lactamase with a non-reactive residue on the Ω-loop replaced by a reactive residue.

BRIEF DESCRIPTION OF THE DRAWINGS

Preferred embodiments of the present invention will now be explained by way of example and with reference to the accompany drawings in which.

DETAILED DESCRIPTION OF THE PREFERRED EMBODIMENT

Figure 1:
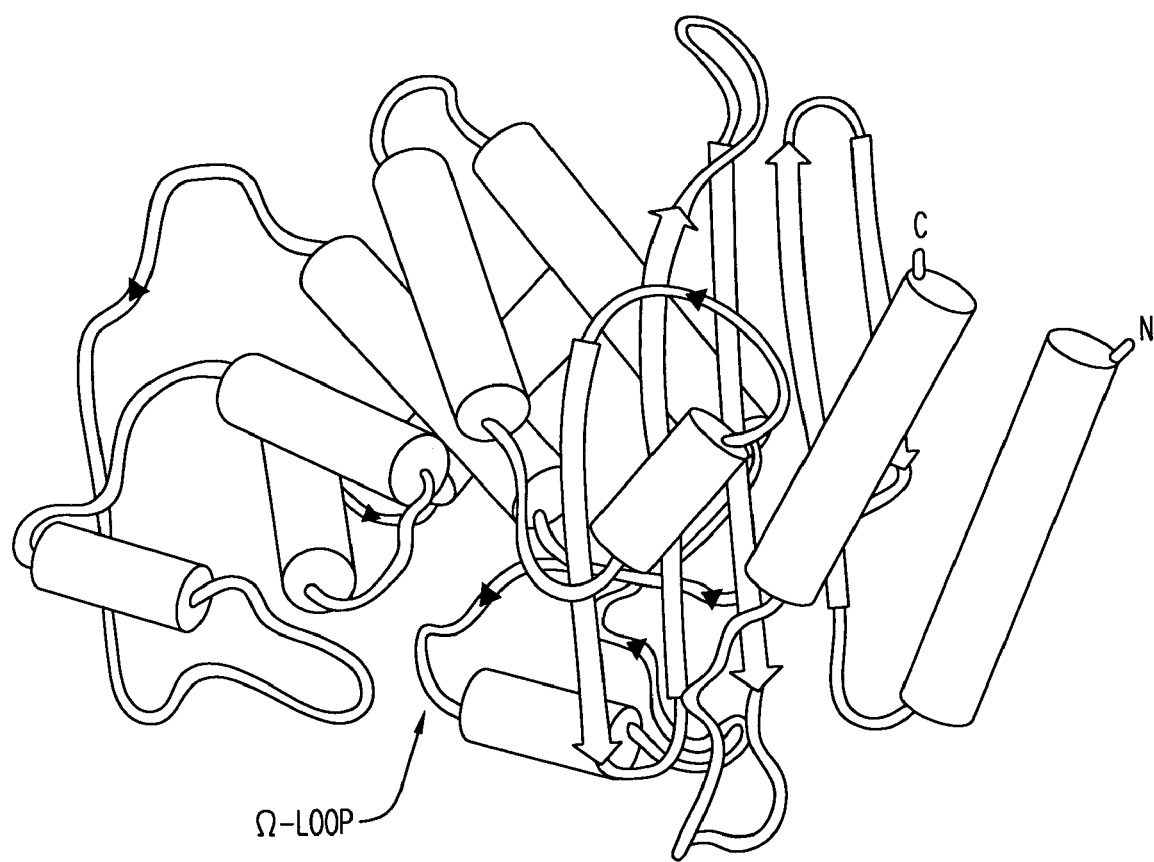
FIG. 1 shows the tertiary structure of β-lactamase I.

This invention is now described by way of example with reference to the figures in the following paragraphs.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

One way to satisfy the objects mentioned above is to develop a biosensor by incorporating a reporter group or indicator molecule (e.g. luminescent probes) into a biomolecule (e.g. β-lactamase or any penicillin binding proteins) such that the reporter group can transform the substrate or inhibitor-binding event into a measurable signal. This can be achieved by incorporating a reactive residue, for example thiol-containing cysteine, into a protein by site-directed mutagenesis, and then labeling the cysteine residue with an indicator molecule, for example a thiol-reactive reporter group. Such biosensors offer a number of advantages, including high sensitivity, high specificity, simplicity and low cost. However, this approach requires that the attached indicator molecule must not impair the binding affinity of the protein to a great extent to provide a higher sensitivity.

The structure and amino acid sequence of β-lactamase can be found in the following References 1 to 5, respectively:
1. Madgwick, P. J. and Waley, S. G. β-lactamase I from *Bacillus cereus*. Structure and site-directed mutagenesis (1987) *Biochem. J.* 248, 657-662.
2. Aschaffenburg, R., Phillips, D. C, Sutton, B. J., Baldwin, G., Kiener, P. A., Waley, S. G. Preliminary crystallographic data for β-lactamase I from *Bacillus cereus* 569. (1978) *J. Mol. Biol.* 120, 447-449.
3. Samraoui, B., Sutton, B. J., Todd, R. J., Artymiuk, P. J., Waley, S. G., Phillips, D. C. Tertiary structural similarity between a class A β-lactamase and a penicillin-sensitive D-anlanyl carboxypeptidase-transpeptidase. (1986) *Nature* 320, 378-380.
4. Moews, P. C., Knox, J. R., Dideberg, O., Charlier, P., Frere, J. M., β-lactamase *Bacillus licheniformis* 749/C at 2 Å resolution. (1990) *Proteins* 7, 156-171.
5. Ambler, R. P.; Coulson, A. F. W, Frere, J.-M.; Ghuysen, J.-M.; Joris, B.; Forsman, M.; Levesque, R. C.; Tiraby, G.; Waley, S. G. A standard numbering scheme for the Class A β-lactamase, (1991), *Biochem. J.* 276, 269-272.

In this invention, a biosensor for β-lactam antibiotics and β-lactamase inhibitors is provided by attaching an indicator molecule close to the active site of a β-lactamase. In a specific embodiment of this invention, the indicator molecule is an environmentally sensitive fluorescein molecule, and the β-lactamase is a mutant. The mutant (E166C) was constructed in which a residue on the Ω-loop of the wild-type β-lactamase I was replaced by a reactive residue by site-directed mutagenesis. The reactive residue can be any residue having a free function group to react with an indicator molecule. For example, amino acids containing a free alcohol group such as serine, threonine and tyrosine may be used. These amino acids can be derivatised with salicylaldehyde, which can then be coupled to fluorescent reagents such as 1,2-diamino-4,5-dimethoxybenzene. Amino acids containing a free carboxylic acid group such as glutamic acid and aspartic acid may also be used, which can be coupled to carbodiimides which then react with a fluorescent reagent, or to carbodiimides which contain a fluorophore. A further option is to use amino acids containing a free amine group such as lysine, which can be coupled to isothiocyanantes or succinimidyl esters.

In one specific embodiment, the replaced residue is the Glu-166 residue (according to the ABL number system, Reference 5), and the reactive residue is a cysteine residue. The mutant was then labeled with an indicator molecule, in one specific embodiment a thiol-reactive fluorescein-5-maleimide, at its reactive residue, the cysteine residue, to form E166Cf, a specific modified β-lactamase of this invention.

It should be emphasized that this invention shall not be limited by the E166Cf constructed. The reside to be replaced on the Ω-loop of the wild-type β-lactamase can be at various positions including Asn163, Arg164, Phe165, Glu166, Thr167, Glu168, Leu169, Asn170, Glu171, Ala172, Ile173, Pro174, Gly175, Asp176, Ile177, Arg178, though preferably to be the Glu-166 residue. Further, residues outside the Ω-loop but close to the active site can also be used, e.g. Ser70, Lys73, Asp104, Ser130, and Lys234. The β-lactamase can be wild type β-lactamase or its mutant, whether it is a singly or multiply mutated mutant, in which a single mutated mutant contains only one amino acid substitution while a multiply mutated mutant contains more than one amino acid substitutions. Further, the indicator molecule can be any other molecule capable of emitting a detectable signal other than fluorescent signal. However, fluorophore capable of emitting fluorescent signal as fluorescent signal may create less influence to the structure of the enzyme.

Referring to the specific E166Cf, as the wild-type β-lactamase I has no cysteine, incorporation of a cysteine residue into the protein allows the fluorophore to be specifically attached at the desired site. The Glu-166 residue was chosen as the labeling site not only because of its closeness to the enzyme's active site, but also the flexibility of the Ω-loop which allows the attached fluorescein molecule to move when a substrate enters the active site. Thus, the E166Cf mutant can serve as a reagentless tool to detect β-lactam antibiotics with high sensitivity and specificity. Moreover, substrate competition between the labeled enzyme (E166Cf) and bacterial β-lactamase will lead to a change in antibiotic concentration (e.g. decrease in antibiotic concentration due to the hydrolytic action of bacterial β-lactamase) and hence generating different fluorescence signals, thus allowing the labeled enzyme to be used conveniently in drug screening, selecting the most appropriate β-lactam antibiotic for patients with bacterial infection.

The synthesis of E166Cf and its use in detecting β-lactam antibiotics and β-lactamase inhibitors, and/or in screening bacteria for β-lactamases against a panel of β-lactam antibiotics will now be described in details. However, as there are various options in designing the modified β-lactamase as mentioned above, suitable modifications may be necessary to the below methods, which are readily available to a person skilled in the art.

Expression and purification of wild-type β-lactamase I and E166C mutant were performed as described previously (Reference 6: Leung, Y. C. Robinson, C. V., Alpin, R. T., Waley, S. G., Site-directed synthesis of β-lactamase I: role of Glu-166 (1994) *Biochem. J.* 299, 671-678). with slight modifications. Both wild-type β-lactamase I and E166C mutant were expressed in *B. subtilis* 1A304 (φ105MU331). A bacterial strain was streaked on an agar plate containing 5 μg/ml chloramphenicol, and the plate was incubated at 37° C. for 24 h. A single bacterial colony from the agar plate was inoculated into 100 ml of sterilized BHY medium (37 g/l brain heart infusion and 5 g/l yeast extract) containing 5 μg/ml chloramphenicol, which was then incubated at 37° C. with shaking at 300 rpm overnight. About 2 ml of overnight inoculum was added to each of four conical flasks containing 100 ml of sterilized BHY medium. The inoculated media were then incubated at 37° C. with shaking at 300 rpm. When the $OD_{600}$ reached 3.5-4.0, the bacterial cultures were heated in a water bath at 51° C. for 5 min and then incubated at 37° C. with shaking at 300 rpm for a further 6 h. The supernatant of the bacterial cultures was collected by centrifugation (9000 rpm) at 4° C. for 25 min, and adjusted to pH 7.0 with conc. HCl. The β-lactamases were extracted by mixing the supernatant with 40 g of celite 545 for 30 min in an ice bath. After discarding the supernatant, the celite was washed three to four times with 300 ml of deionized water. The β-lactamases were collected by mixing the celite three times with 100 ml of protein elution buffer (100 mM Tris-HCl, 2 M NaCl and 100 mM tri-sodium citrate, pH 7.0). The protein solution was filtered by suction and then concentrated to 10 ml at 4° C. using a concentrator (Amicon)

equipped with a piece of YM-1 membrane (MWCO=1,000). The concentrated protein solution was exchanged with 20 mM $NH_4HCO_3$ and then freeze-dried. The enzyme powder was stored at −80° C. About 15 mg of wild-type β-lactamase I and 20 mg of E166C mutant were obtained by the above procedures.

Protein Labeling

About 2.5 mg of E166C mutant was dissolved in 4 ml of 6 M guanidine hydrochloride. The protein solution was incubated at room temperature for 30 min to unfold the mutant. A ten-fold molar excess of fluorescein-5-maleimide (purchased from Molecular Probes) dissolved in dimethylsulfoxide was added to the protein solution, and the pH of the mixture was adjusted to 7.5 with 0.2 M NaOH. The mixture was stirred at room temperature for 2 h in dark, and then dialyzed with a dialysis tubing (MWCO=12,000) against 1 L of 20 mM $NH_4HCO_3$ (pH 7.0) at 4° C. for about 3 days to remove the free dyes. Buffer exchanges were carried out regularly during dialysis. After dialysis, the labeled mutant (E166Cf) was freeze-dried and stored at −80° C.

Characterization of the E166Cf Enzyme

Figure 2A:
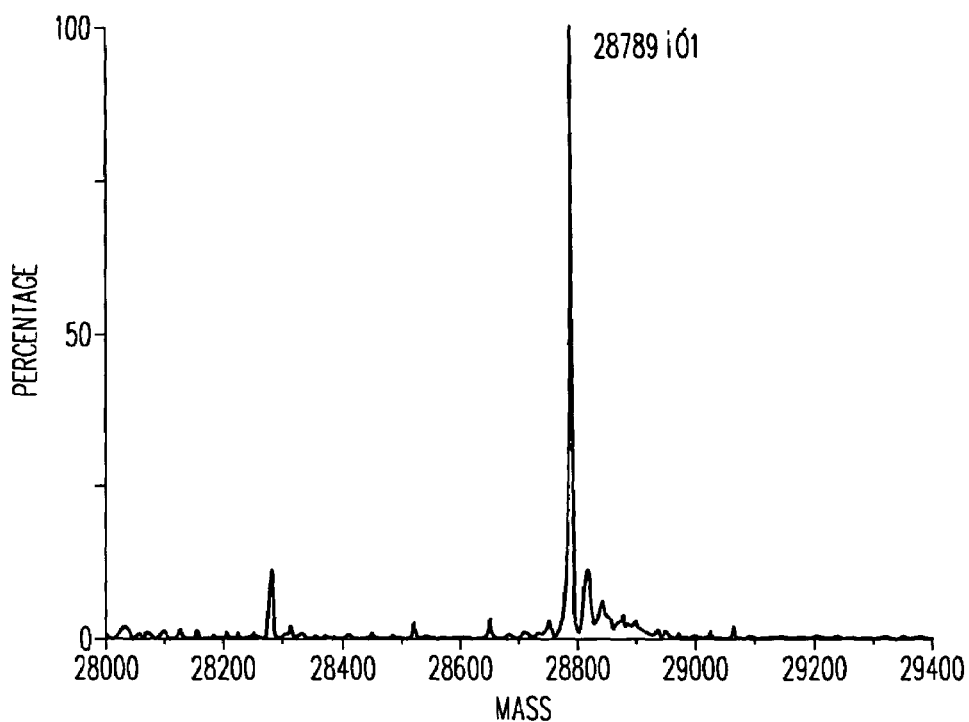
FIG. 2 shows the ESI mass spectrum of (A) E166C and (B) E166Cf mutants.
Figure 2B:
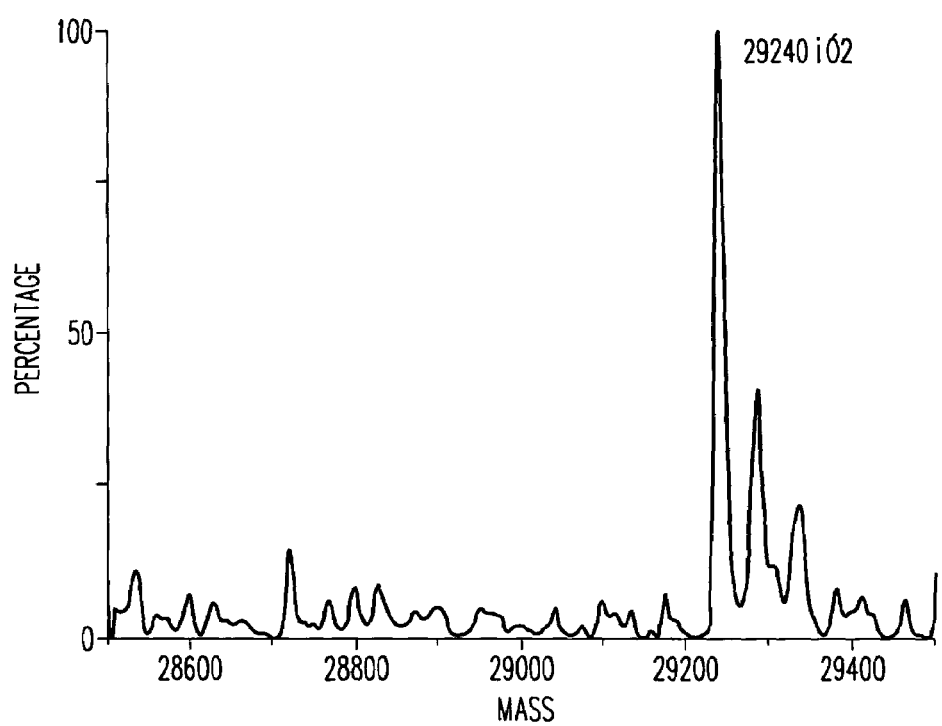

The labeling of the E166C mutant with fluorescein-5-maleimide was monitored by electrospray ionization mass spectrometry (ESI/MS). The mass spectrometric measurements were performed on a VG Platform mass spectrometer (Micromass) equipped with an electrospray interface. Protein samples (20 µl) were injected into the electrospray source via a loop injector as solution in $H_2O/CH_3CN$ (1:1) containing formic acid (0.2%, v/v). The mass difference between the E166C and E166Cf mutants (FIG. 2) is consistent with the molecular mass of fluorescein-5-maleimide (MW=427) plus the mass of a sodium ion. The mass spectrum of the E166Cf enzyme indicate that almost all the E166C mutants were labeled with fluorescein molecules.

Figure 3:
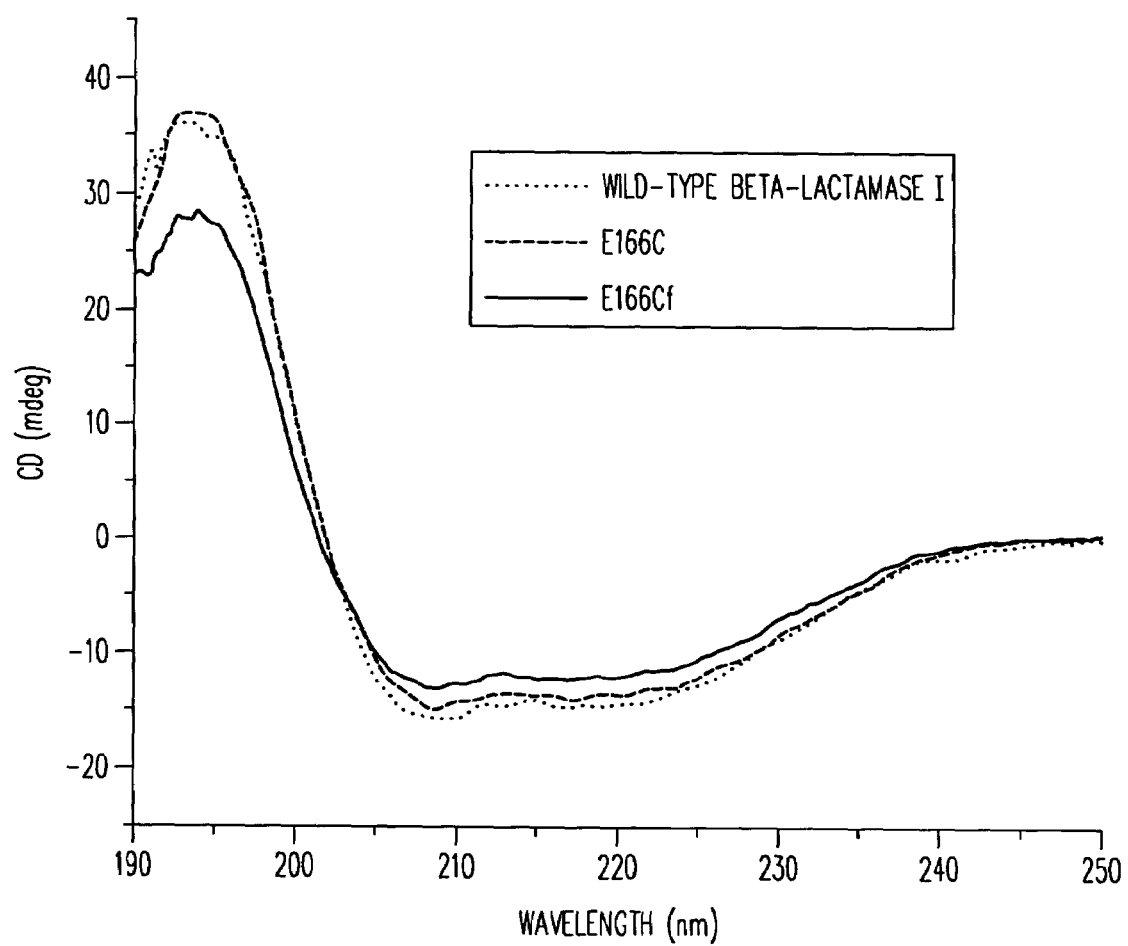
FIG. 3 shows the CD spectra of the wild-type β-lactamase I, E166C and E166Cf mutants at the same concentration ($6.0 \times 10^{-6}$ M) in 50 mM phosphate buffer (pH 7.0)

The secondary structure of the wild-type β-lactamase I, E166C and E166Cf were investigated by circular dichroism (CD) spectropolarimetry. The CD measurements were performed on a Jasco J810 Spectropolarimeter (Jasco Co.). The CD spectra of the wild-type β-lactamase I, E166C and E166Cf mutants at the same concentration ($6.0 \times 10^{-6}$ M) in 50 mM phosphate buffer (pH 7.0) on the far-UV region are shown in FIG. 3. The CD signals exhibit no significant difference, indicating that the secondary structure of the E166Cf enzyme is conserved after labeling with fluorescein.

The hydrolytic activities of the wild-type β-lactamase I, E166C and E166Cf mutants towards penicillin G, penicillin V and ampicillin (Sigma) were monitored by the spectrophotometric method. The spectrophotometric measurements were performed on a Perkin Elmer Lambda Bio20 UV/Vis spectrometer. Substrate hydrolysis was monitored at a fixed wavelength: 235 nm for ampicillin, 232 nm for penicillin G and penicillin V. The initial rate of substrate hydrolysis occurring within 5 min was determined in duplicate at each of 6 different substrate concentrations in 50 mM potassium phosphate buffer (pH 7.0) at 20° C. The initial rates determined were then treated as described in Reference 5 to calculate the Michaelis constants ($K_m$) and turnover numbers ($k_{cat}$) using non-linear regression analysis (equation 1):

$$v = \frac{V_{max} \cdot [S]}{K_m + [S]} \quad (1)$$

where v is the initial rate of substrate hydrolysis, $V_{max}$ the maximum rate of reaction, [S] the initial substrate concentration, $K_m$ the Michaelis constant and $k_{cat}=V_{max}/[\text{Enzyme}]$.

The measured steady-state kinetic parameters for hydrolysis of penicillin G, penicillin V and ampicillin by the wild-type β-lactamase I, E166C and E166Cf mutants are summarized in Table 1. The results indicate that the hydrolytic activity of the labeled enzyme is conserved after labeling with fluorescein.

TABLE 1

| | $K_m$ (µM) | | |
| --- | --- | --- | --- |
| | Wild-type | E166C | E166Cf |
| Penicillin G | 48 ± 3 | 72 ± 3 | 213 ± 11 |
| Penicillin V | 52 ± 4 | 71 ± 6 | 117 ± 10 |
| Ampicillin | 142 ± 8 | 306 ± 30 | 262 ± 31 |

| | $k_{cat}$ (s$^{-1}$) | | |
| --- | --- | --- | --- |
| | Wild-type | E166C | E166Cf |
| Penicillin G | 2612 ± 320 | 2.07 ± 0.02 | 5.28 ± 0.09 |
| Penicillin V | 2109 ± 4 | 1.53 ± 0.03 | 2.97 ± 0.06 |
| Ampicillin | 5213 ± 275 | 4.1 ± 0.1 | 6.2 ± 0.2 |

| | $k_{cat}/K_m$ (µM$^{-1}$s$^{-1}$) | | |
| --- | --- | --- | --- |
| | Wild-type | E166C | E166Cf |
| Penicillin G | 54 ± 10 | 0.029 ± 0.002 | 0.025 ± 0.002 |
| Penicillin V | 41 ± 4 | 0.021 ± 0.002 | 0.025 ± 0.003 |
| Ampicillin | 37 ± 4 | 0.013 ± 0.002 | 0.023 ± 0.004 |

Fluorescence Measurements of the E166Cf Enzyme in the Presence of Penicillins and Cephalosporins Fluorescence measurements of the E166Cf enzyme in the presence of penicillin G, penicillin V, ampicillin, cefuroxime, cefoxitin and moxalactam were performed on a Perkin Elmer LS50B spectrofluorometer. For time-resolved fluorescence measurement, excitation and emission wavelengths were set at 494 and 515 nm respectively. Both excitation and emission slit widths were set at 5 nm. All fluorescence measurements were performed at room temperature.

Figure 4:
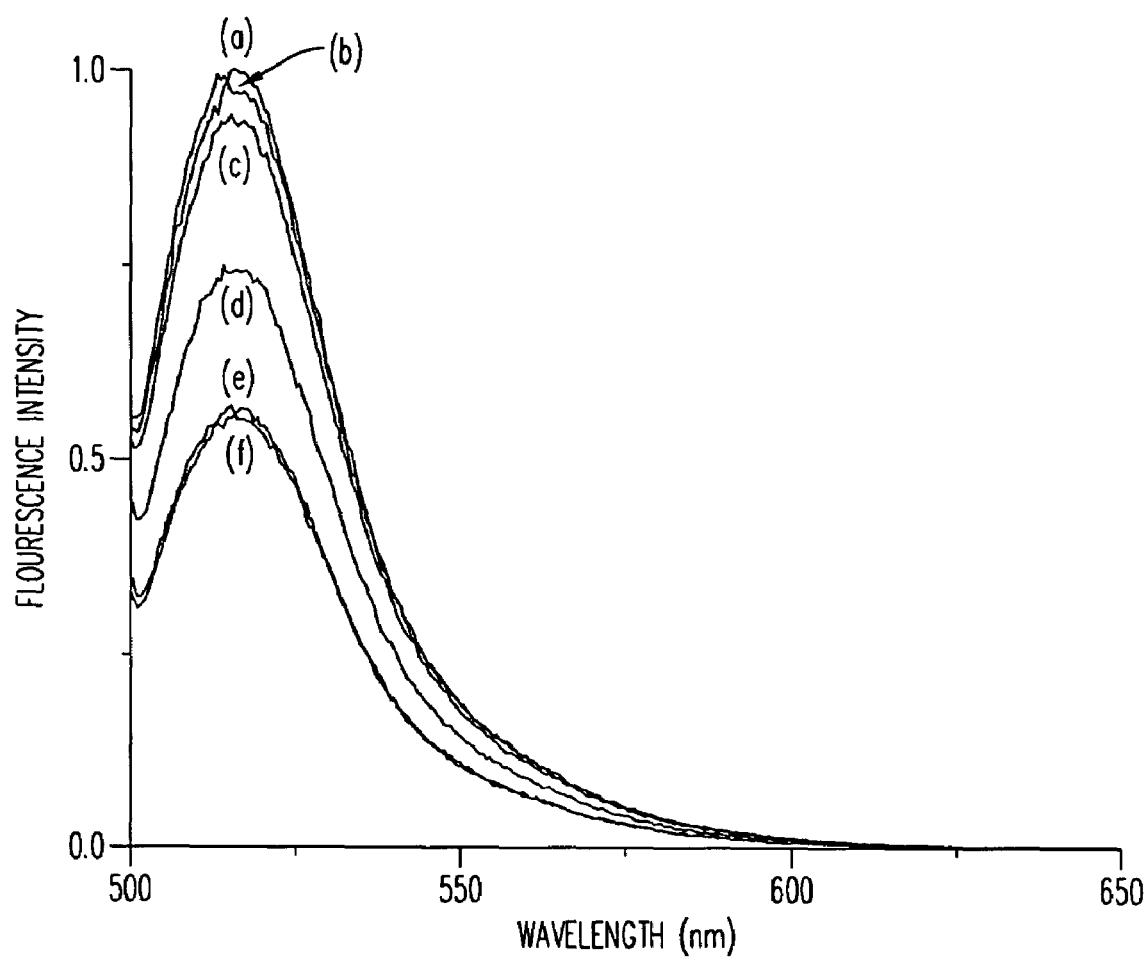
FIG. 4 shows the Fluorescence spectra of the E166Cf enzyme ($1.2 \times 10^{-7}$ M) in 50 mM phosphate buffer (pH 7.0) in the presence of $1.0 \times 10^{-4}$ M penicillin G (a), $1.0 \times 10^{-5}$ M penicillin G (b), $1.0 \times 10^{-6}$ M penicillin G (c), $1.0 \times 10^{-7}$ M penicillin G (d), $1.0 \times 10^{-8}$ M penicillin G (e) and 0 M penicillin G (f). The E166Cf enzymes were incubated with various concentrations of penicillin G for 130 s at room temperature before measurement. Excitation wavelength: 494 nm.
Figure 5:
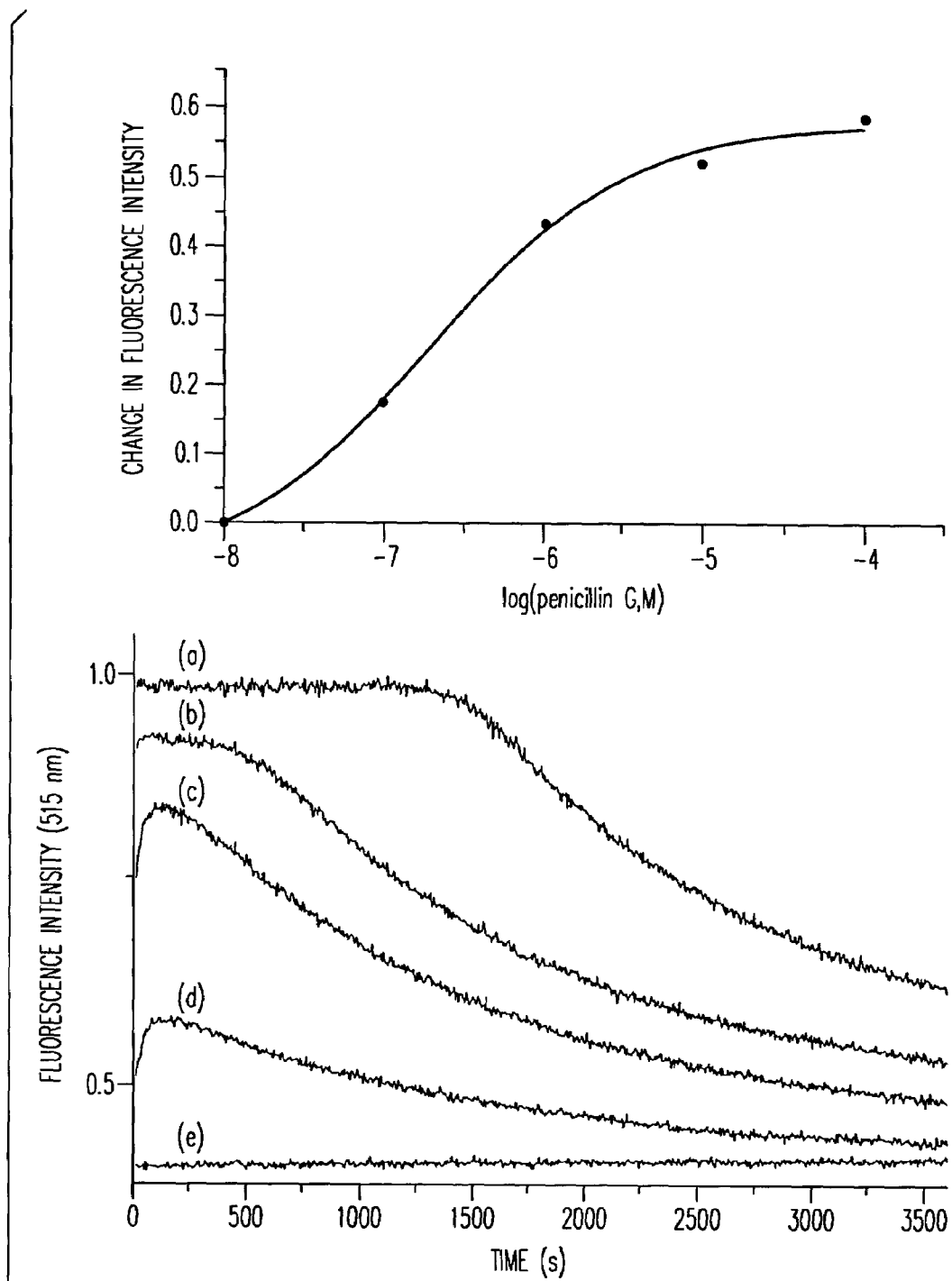
FIG. 5 shows the Time-resolved fluorescence measurements of the E166Cf enzyme ($1.2 \times 10^{-7}$ M) at 515 nm in 50 mM phosphate buffer (pH 7.0) in the presence of $1.0 \times 10^{-4}$ M penicillin G (a), $1.0 \times 10^{-5}$ M penicillin G (b), $1.0 \times 10^{-6}$ M penicillin G (c), $1.0 \times 10^{-7}$ M penicillin G (d) and $1.0 \times 10^{-8}$ M penicillin G (e). Excitation wavelength: 494 nm. The inset shows the plot of the change in fluorescence intensity (at the peak maxima) versus log (penicillin G, M)
Figure 6:
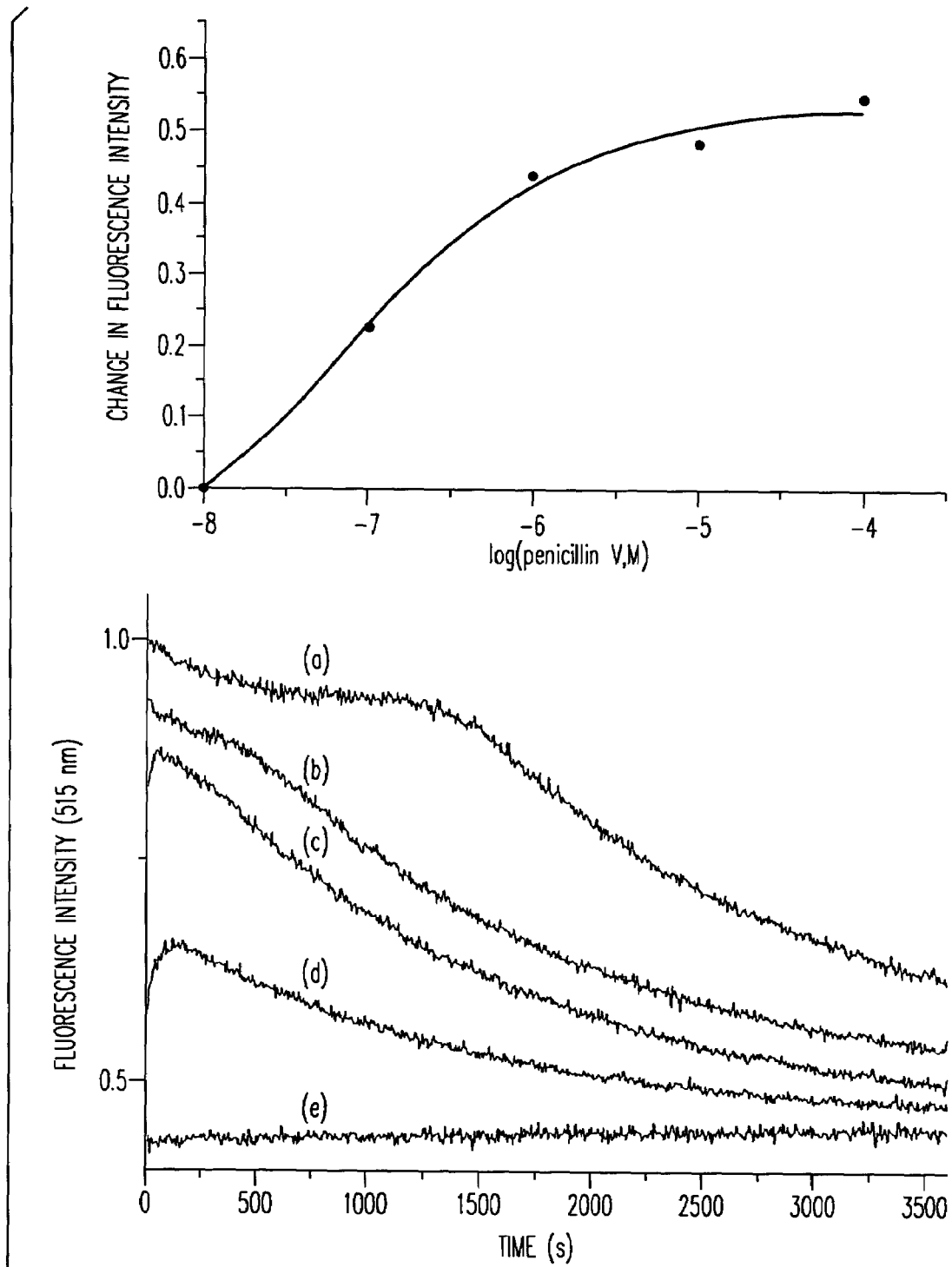
FIG. 6 shows the time-resolved fluorescence measurements of the E166Cf enzyme ($1.2 \times 10^{-7}$ M) at 515 nm in 50 mM phosphate buffer (pH 7.0) in the presence of $1.0 \times 10^{-4}$ M penicillin V (a), $1.0 \times 10^{-5}$ M penicillin V (b), $1.0 \times 10^{-6}$ M penicillin V (c), $1.0 \times 10^{-7}$ M penicillin V (d) and $1.0 \times 10^{-8}$ M penicillin V (e). Excitation wavelength: 494 mn. The inset shows the plot of the change in fluorescence intensity (at the peak maxima) versus log (penicillin V, M)
Figure 7:
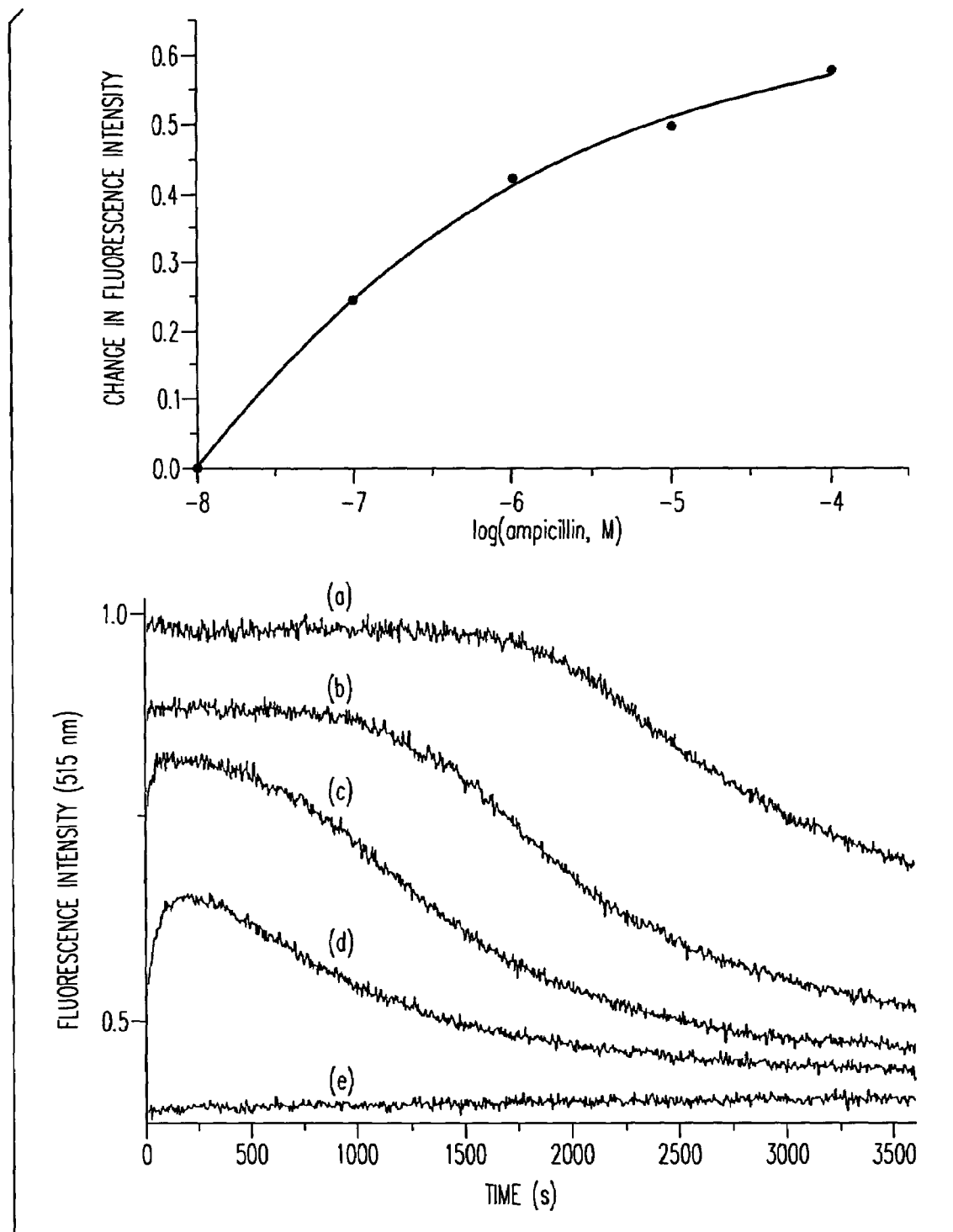
FIG. 7 shows the time-resolved fluorescence measurements of the E166Cf enzyme ($1.2 \times 10^{-7}$ M) at 515 nm in 50 mM phosphate buffer (pH 7.0) in the presence of $1.0 \times 10^{-4}$ M ampicillin (a), $1.0 \times 10^{-5}$ M ampicillin (b), $1.0 \times 10^{-6}$ M ampicillin (c), $1.0 \times 10^{-7}$ M ampicillin (d) and $1.0 \times 10^{-8}$ M ampicillin (e). Excitation wavelength: 494 nm. The inset shows the plot of the change in fluorescence intensity (at the peak maxima) versus log (ampicillin, M)

With penicillin G as substrate, the fluorescence signal of the E166Cf enzyme ($1.2 \times 10^{-7}$ M) at 515 nm in 50 mM phosphate buffer (pH 7.0) increases as a function of the antibiotic concentration (FIG. 4). The time-resolved fluorescence signals of the E166Cf enzyme at 515 nm were also measured with various concentrations of penicillin G (FIG. 5). At low antibiotic concentration ($1.0 \times 10^{-7}$ and $1.0 \times 10^{-6}$ M), the fluorescence intensity of the E166Cf enzyme increases gradually and then declines. At high antibiotic concentration ($1.0 \times 10^{-5}$ and $1.0 \times 10^{-4}$ M), the fluorescence signal increases instantaneously and levels off to a plateau. The fluorescence signal stays at the plateau for a certain length of time and then declines afterwards. Similar results were obtained with penicillin V and ampicillin (FIGS. 6 and 7).

Figure 8:
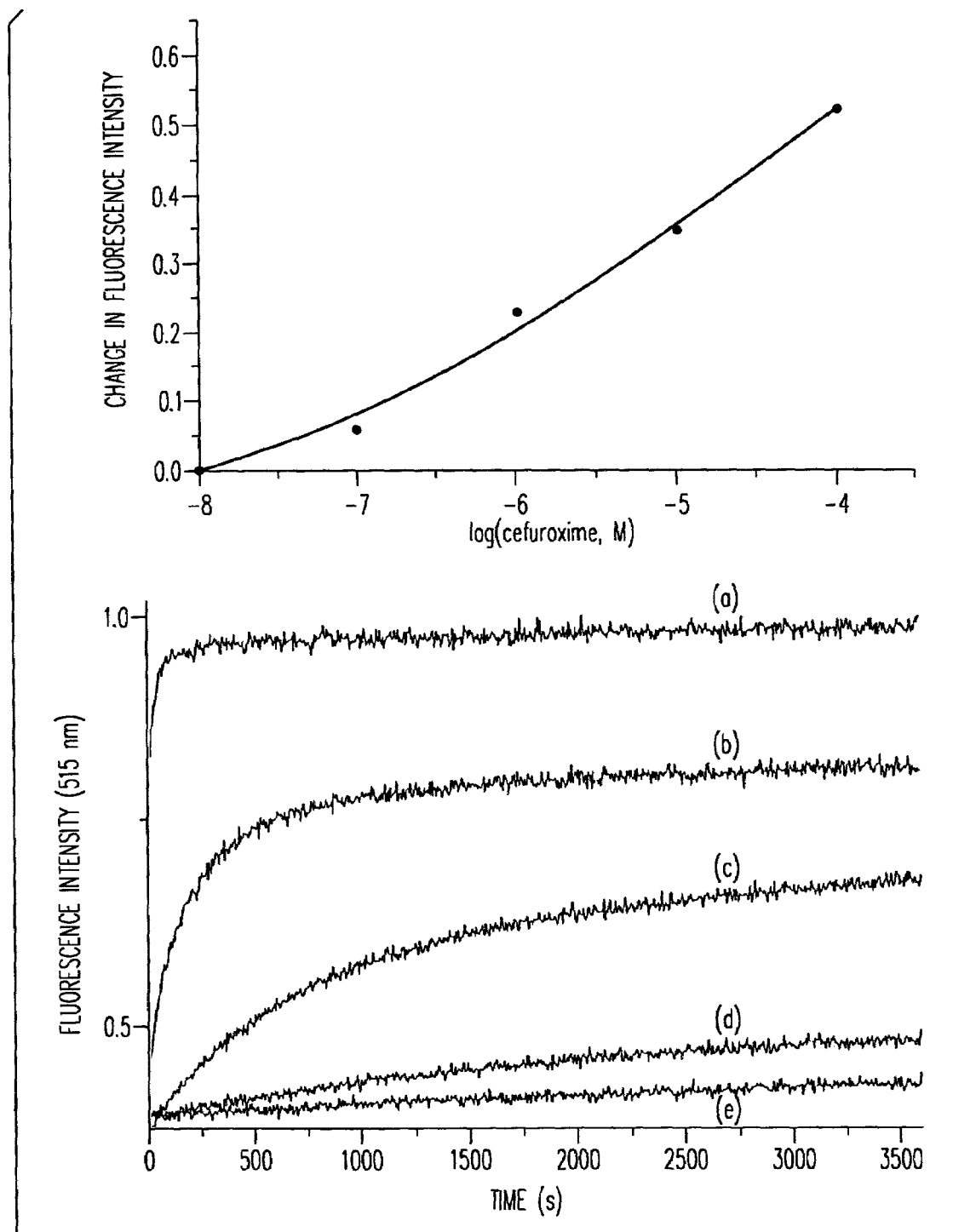
FIG. 8 shows the time-resolved fluorescence measurements of the E166Cf enzyme ($1.2 \times 10^{-7}$ M) at 515 nm in 50 mM phosphate buffer (pH 7.0) in the presence of $1.0 \times 10^{-4}$ M cefuroxime (a), $1.0\times10^{-5}$ M cefuroxime (b), $1.0\times10^{-6}$ M cefuroxime (c), $1.0\times10^{-7}$ M cefuroxime (d) and $1.0\times10^{-8}$ M cefuroxime (e). Excitation wavelength: 494 nm. The inset shows the plot of the change in fluorescence intensity (at the peak maxima) versus log (cefuroxime, M)
Figure 9:
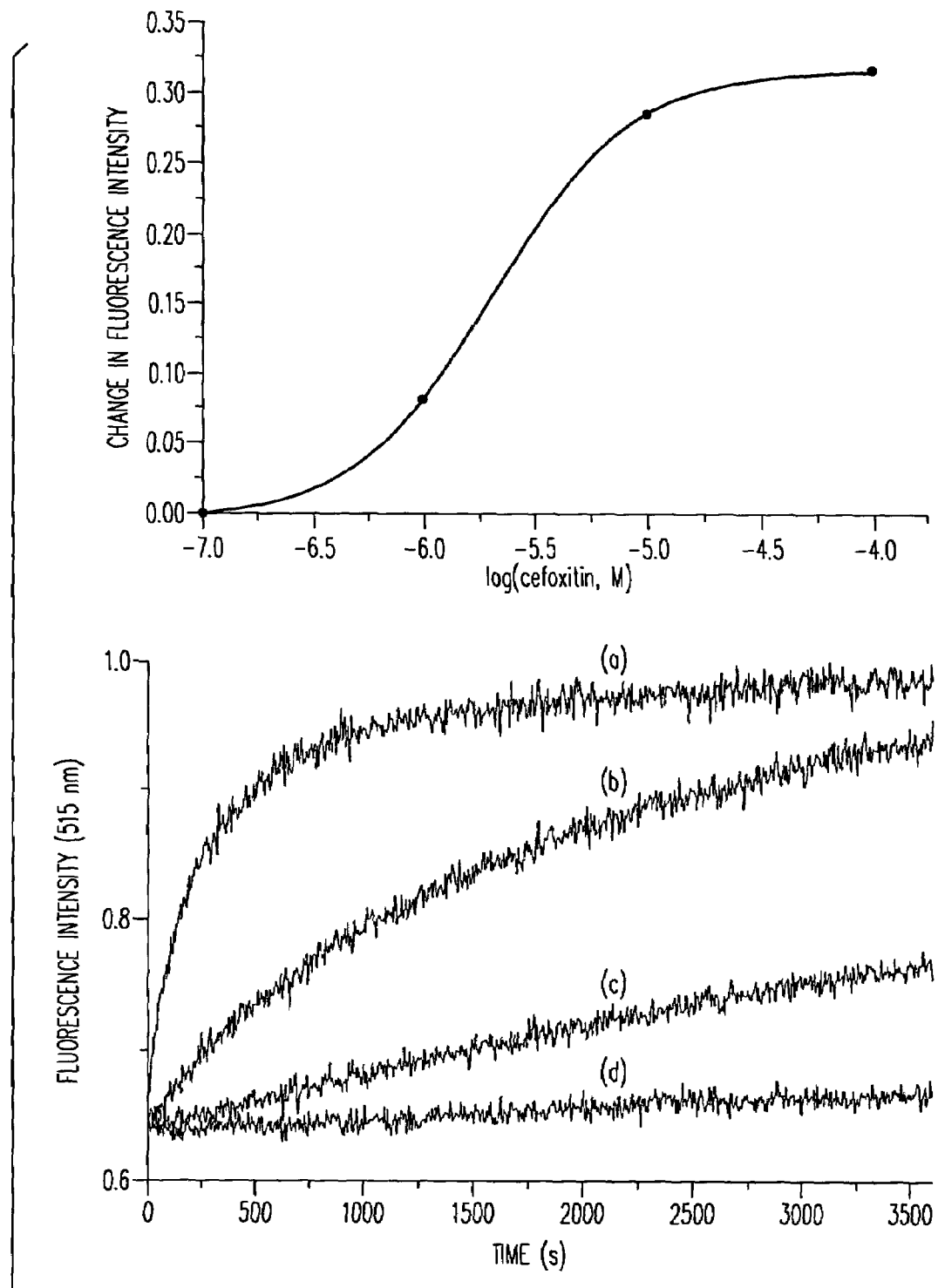
FIG. 9 shows the time-resolved fluorescence measurements of the E166Cf enzyme ($1.2\times10^{-7}$ M) at 515 nm in 50 mM phosphate buffer (pH 7.0) in the presence of $1.0\times10^{-4}$ M cefoxitin (a), $1.0\times10^{-5}$ M cefoxitin (b), $1.0\times10^{-6}$ M cefoxitin (c) and $1.0\times10^{-7}$ M cefoxitin (d). Excitation wavelength: 494 nm. The inset shows the plot of the change in fluorescence intensity (at the peak maxima) versus log (cefoxitin, M)
Figure 10:
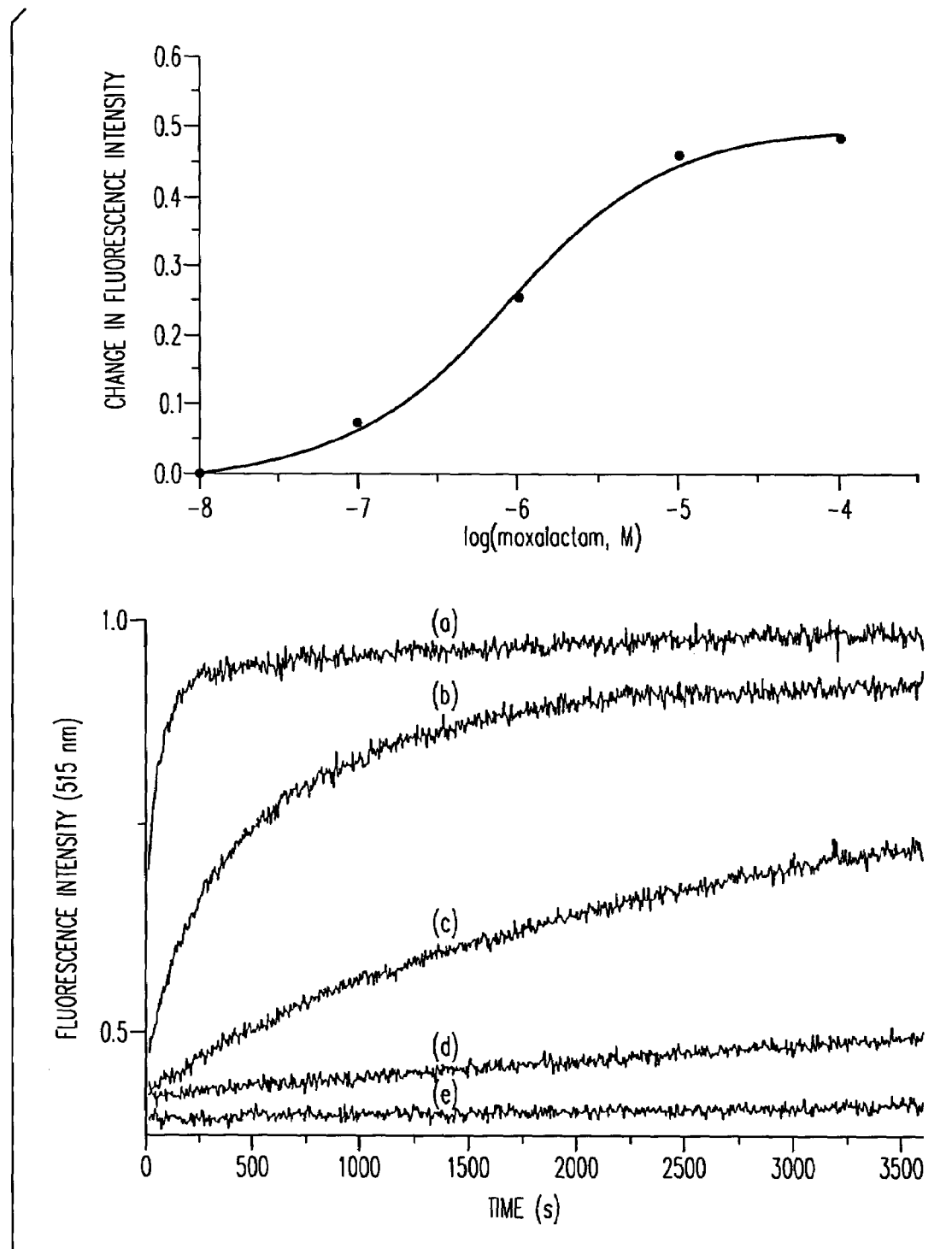
FIG. 10 shows the time-resolved fluorescence measurements of the E166Cf enzyme ($1.2\times10^{-7}$ M) at 515 nm in 50 mM phosphate buffer (pH 7.0) in the presence of $1.0\times10^{-4}$ M moxalactam (a), $1.0\times10^{-5}$ M moxalactam (b), $1.0\times10^{-6}$ M moxalactam (c), $1.0\times10^{-7}$ M moxalactam (d) and $1.0\times10^{-8}$ M moxalactam (e). Excitation wavelength: 494 nm. The inset shows the plot of the change in fluorescence intensity (at the peak maxima) versus log (moxalactam, M)
Figure 11A:
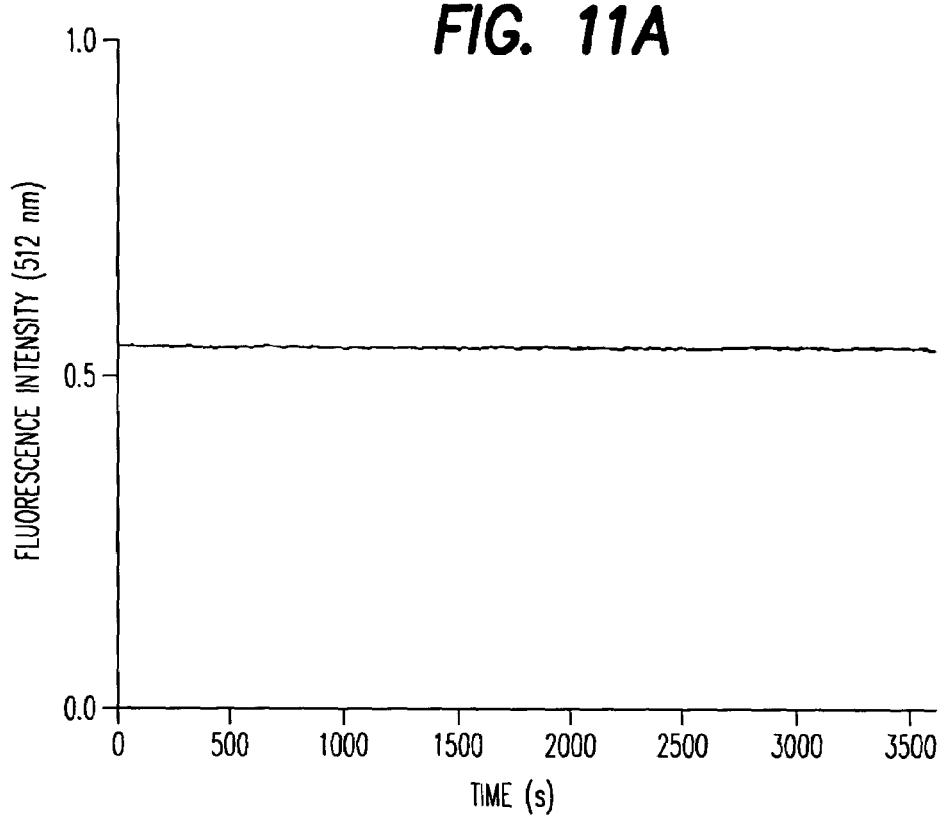
FIG. 11 shows the time-resolved fluorescence measurements of free fluorescein ($1.2\times10^{-7}$ M) at 512 nm in 50 mM phosphate buffer (pH 7.0) in the presence of unlabeled E166C enzyme ($1.2\times10^{-7}$ M) with (A) $1.0\times10^{-5}$ M penicillin G, (B) $1.0\times10^{-5}$ M penicillin V, (C) $1.0\times10^{-5}$ M ampicillin, (D) $1.0\times10^{-5}$ M cefuroxime, (E) $1.0\times10^{-5}$ M cefoxitin and (F) $1.0\times10^{-5}$ M moxalactam as substrates. Excitation wavelength: 494 nm.
Figure 11B:
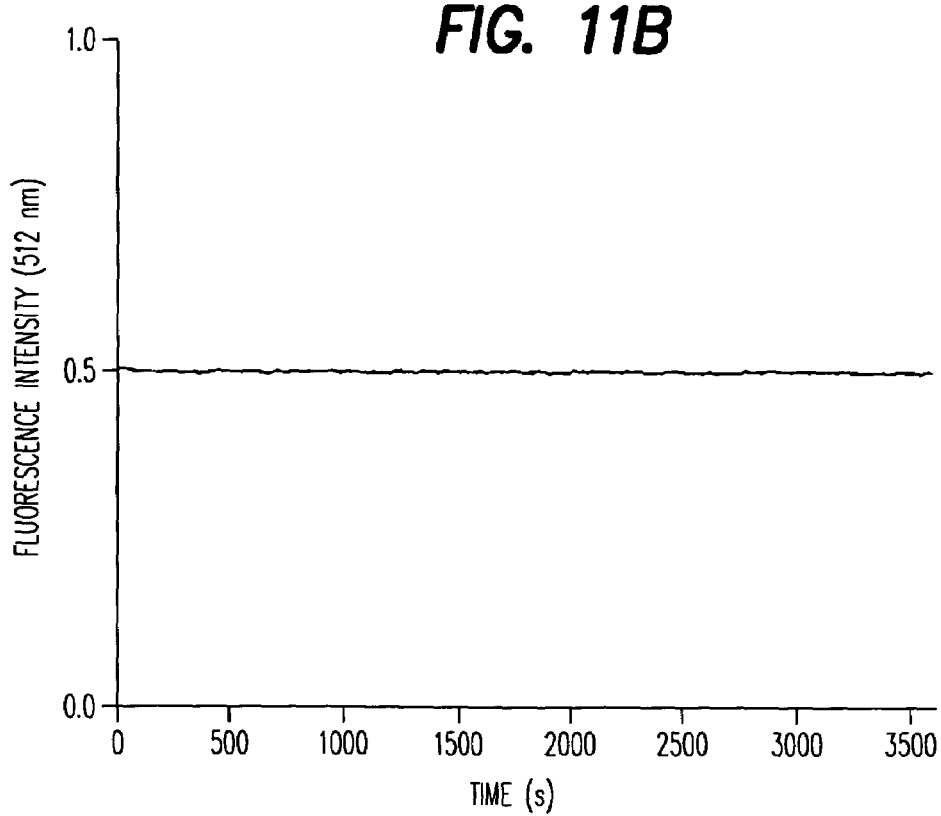
Figure 11C:
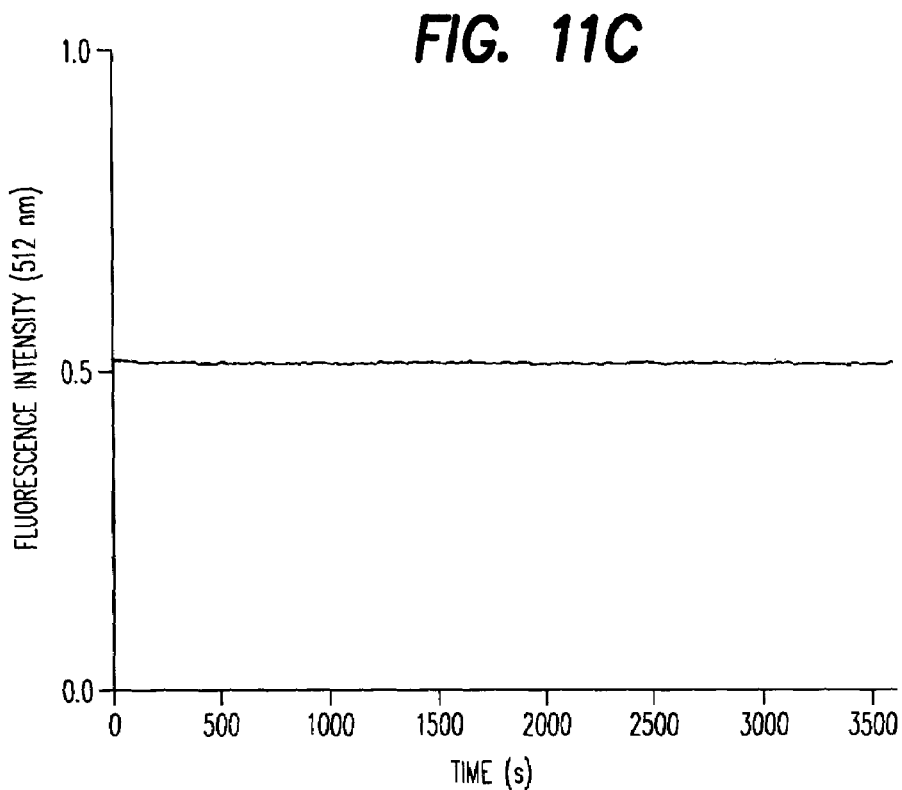
Figure 11D:
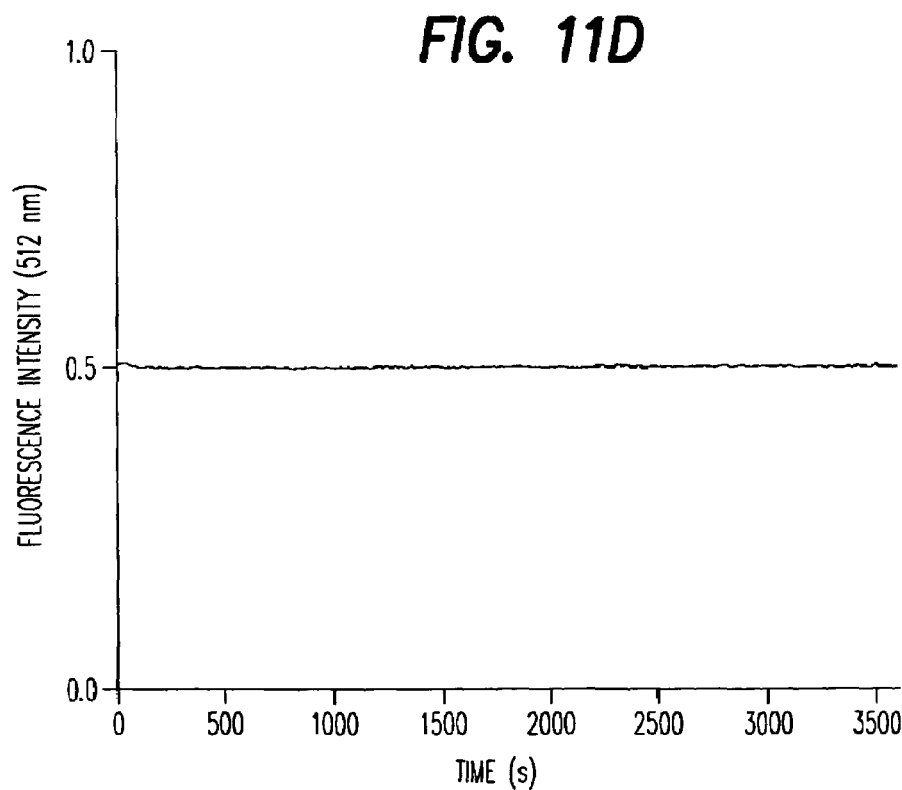
Figure 11E:
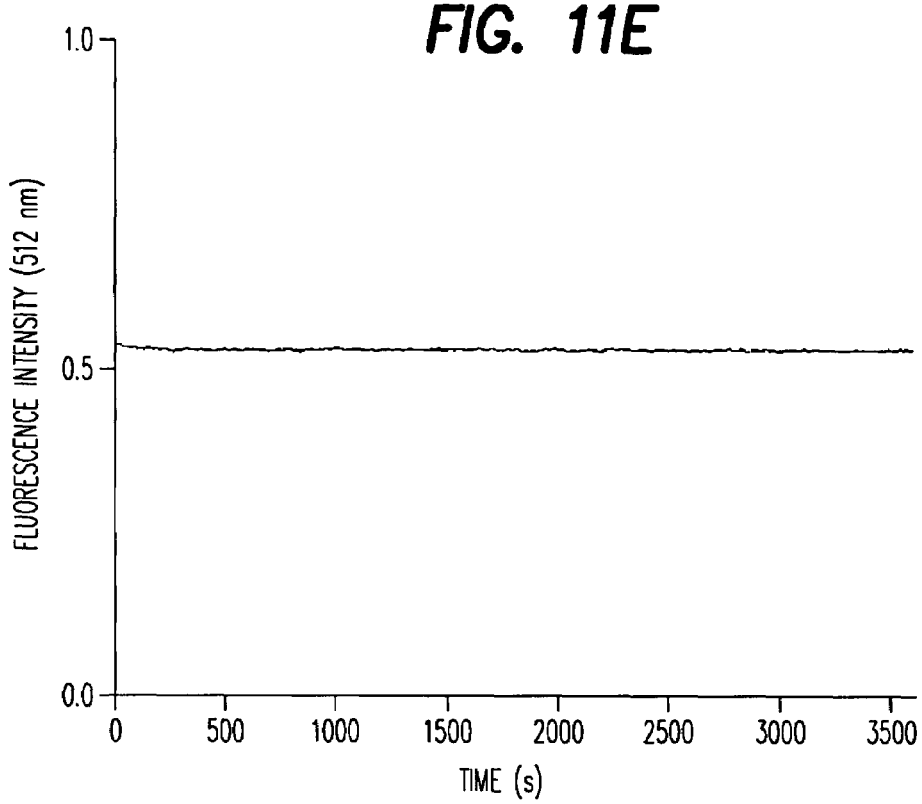
Figure 11F:
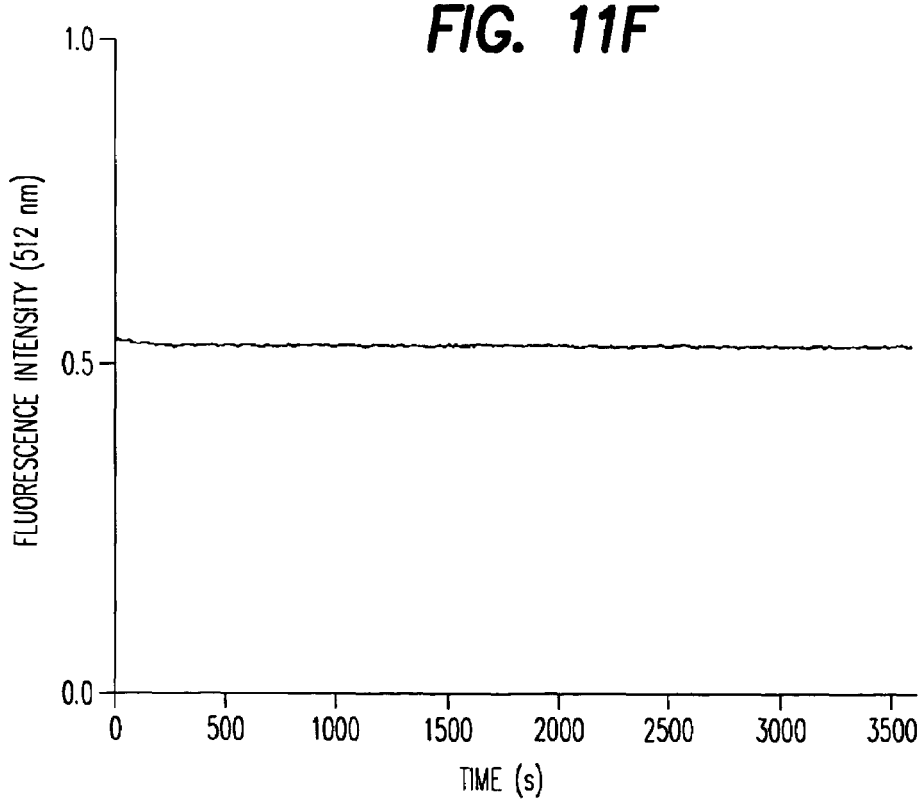

With cefuroxime, cefoxitin and moxalactam as substrates, the fluorescence intensities of the E166Cf enzyme ($1.2 \times 10^{-7}$ M) at 515 nm in 50 mM phosphate buffer (pH 7.0) also increase as a function of antibiotic concentration (FIGS. 8 to 10). The E166Cf enzyme exhibited increasing fluorescence signals with antibiotic concentration, but no subsequent decline in intensity was observed even after one hour.

As the fluorescence intensity of fluorescein is known to change with pH, investigations were also made to see if the observed fluorescence changes were a result of the change in pH upon hydrolysis of the antibiotics by the labeled enzyme. First of all, the fluorescence intensity of fluorescein is known to decrease when the pH is lowered. So the observed increase in fluorescence intensity in the presence of antibiotics is not consistent with the generation of carboxylic acids upon hydrolysis by the enzyme. After the completion of hydrolysis, the overall change in pH of the bulk phosphate buffer solution as monitored by a pH electrode was less than 0.5 pH unit for penicillin G ($1.0 \times 10^{-5}$ M). When the fluorescence intensity of free fluorescein ($1.2 \times 10^{-7}$ M) in 50 mM phosphate buffer (pH 7.0) was measured with penicillin G, penicillin V, ampicillin, cefuroxime, cefoxitin and moxalactam ($1.0 \times 10^{-5}$ M) in the presence of unlabeled E166C enzyme ($1.2 \times 10^{-7}$ M), it remains almost unchanged throughout the whole experiment (FIG. 11) while the E166C enzyme was hydrolyzing the penicillin antibiotics (data not shown). Moreover, cephalosporins, which are known to be poor substrates for the E166C enzyme, also enhance the fluorescence signals. So the possibility that the increase in fluorescence signal of the E166Cf enzyme is due to the change in pH of the bulk solution can be eliminated. Furthermore, the possibility that the observed change in fluorescence signal is due to a change in local pH at the enzyme's active site can also be eliminated because it is unlikely that such a change in pH at the active site takes hundreds to thousands of seconds as shown in the time-resolved fluorescence measurements.

Without any binding theory, the observed fluorescence signals is believed to be attributed to the conformational change in the active site upon substrate binding. Upon binding to antibiotics, the fluorescein label attached to the flexible Ω-loop may move away from the catalytic pocket such that it is well separated from the quenchers (amino acids) in the active site. As a result, the fluorescence of the fluorescein molecule is restored.

The time-resolved fluorescence signals of the E166Cf enzyme obtained in the presence of penicillin and cephalosporin antibiotics at various concentrations can be rationalized by the following three-step model:

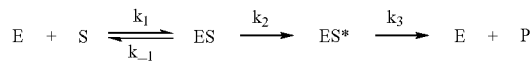

where E is the free β-lactamase enzyme, S the β-lactam substrate, ES a noncovalent enzyme-substrate complex, ES* an acyl-enzyme complex and P the carboxylic acid.

Figure 12:
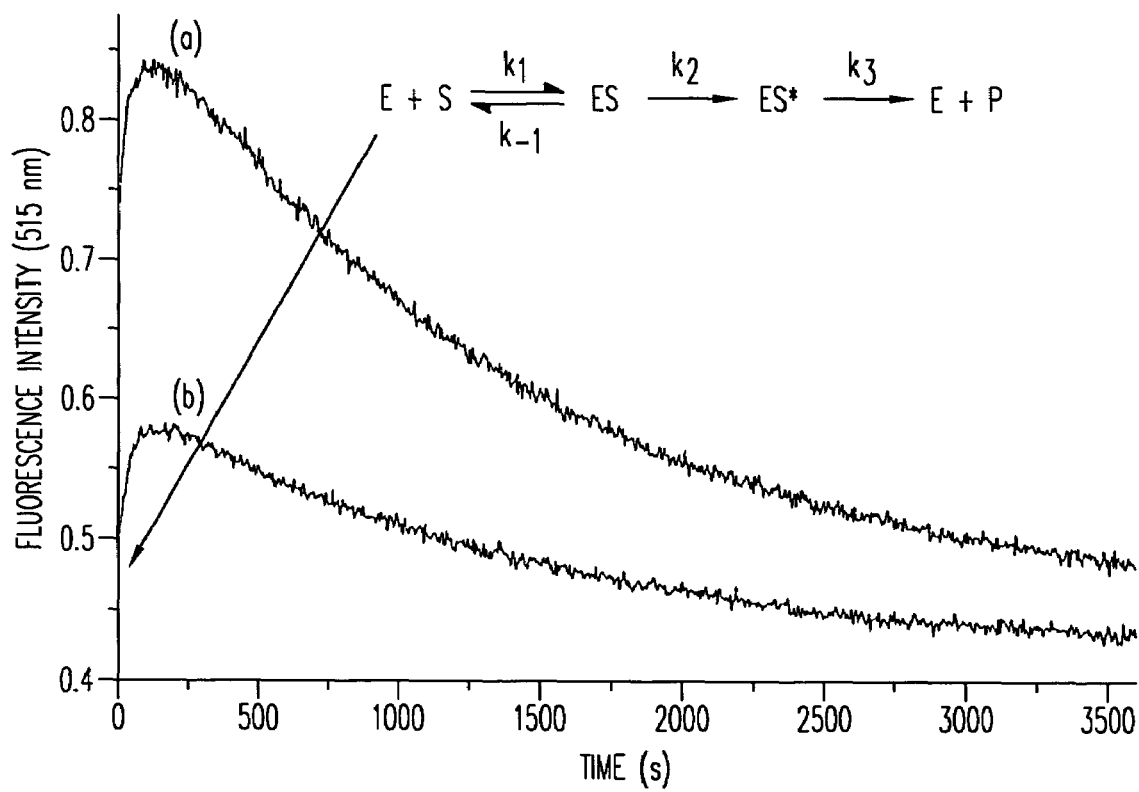
FIG. 12 shows the time-resolved fluorescence measurements of the E166Cf enzyme ($1.2\times10^{-7}$ M) at 515 nm in 50 mM phosphate buffer (pH 7.0) in the presence of $1.0\times10^{-6}$ M penicillin G (a) and $1.0\times10^{-7}$ M penicillin G (b). Excitation wavelength: 494 nm.

At low substrate concentration ($1.0 \times 10^{-7}$ and $1.0 \times 10^{-6}$ M), the binding between the E166Cf enzyme (E) and penicillin substrate (S) would lead to the formation of the ES complex and hence the enhancement in the fluorescence signal. As hydrolysis of antibiotic proceeds, the majority of the penicillin substrates are converted to free carboxylic acids (P). As a result, most of the E166Cf enzymes return to their substrate-free conformation (E) and hence their original weak fluorescence signals were restored (FIG. 12). This may explain the slow decline in fluorescence signal with time after the peak.

Figure 13:
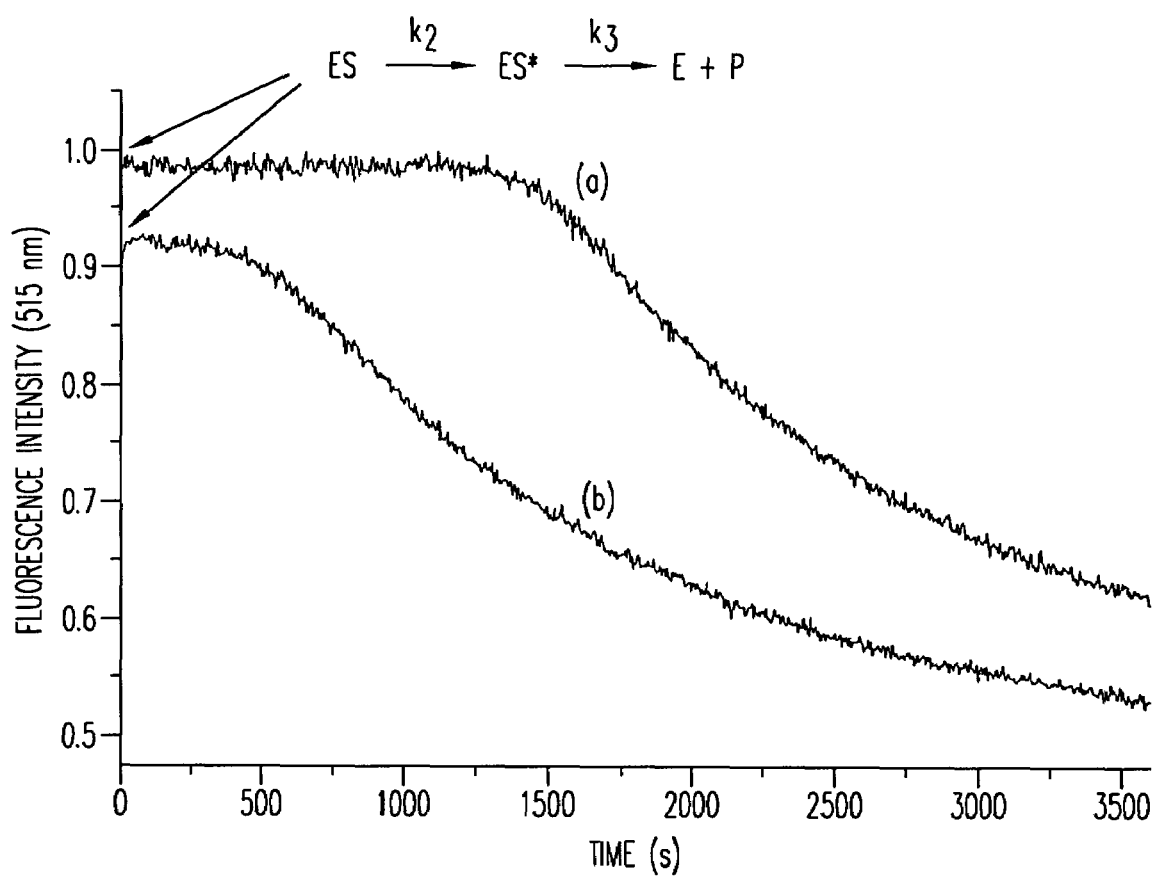
FIG. 13 shows the time-resolved fluorescence measurements of the E166Cf enzyme ($1.2\times10^{-7}$ M) at 515 nm in 50 mM phosphate buffer (pH 7.0) in the presence of $1.0\times10^{-4}$ M penicillin G (a) and $1.0\times10^{-5}$ M penicillin G (b). Excitation wavelength: 494 nm.

At high substrate concentration ($1.0 \times 10^{-5}$ and $1.0 \times 10^{-4}$ M), the penicillin substrates rapidly occupy the active sites to form the ES complexes, thus switching on the fluorescence of the fluorescein labels instantaneously. Because the antibiotic concentration is high, the continuous hydrolysis of antibiotics would maintain the E166Cf enzymes in the ES* state for a while, and hence the fluorescence signal is leveled off to a plateau (FIG. 13). This can be verified by the fact that the 'plateau time' (8 and 22 min for $1.0 \times 10^{-5}$ and $1.0 \times 10^{-4}$ M penicillin G respectively) is consistent with the 'substrate hydrolysis time' determined by spectrophotometric assays (7 and 20 min for $1.0 \times 10^{-5}$ and $1.0 \times 10^{-4}$ M penicillin G respectively). When most of the penicillin substrates have been hydrolyzed to carboxylic acids, the fluorescence signal of the labeled enzyme will decline subsequently.

Figure 14:
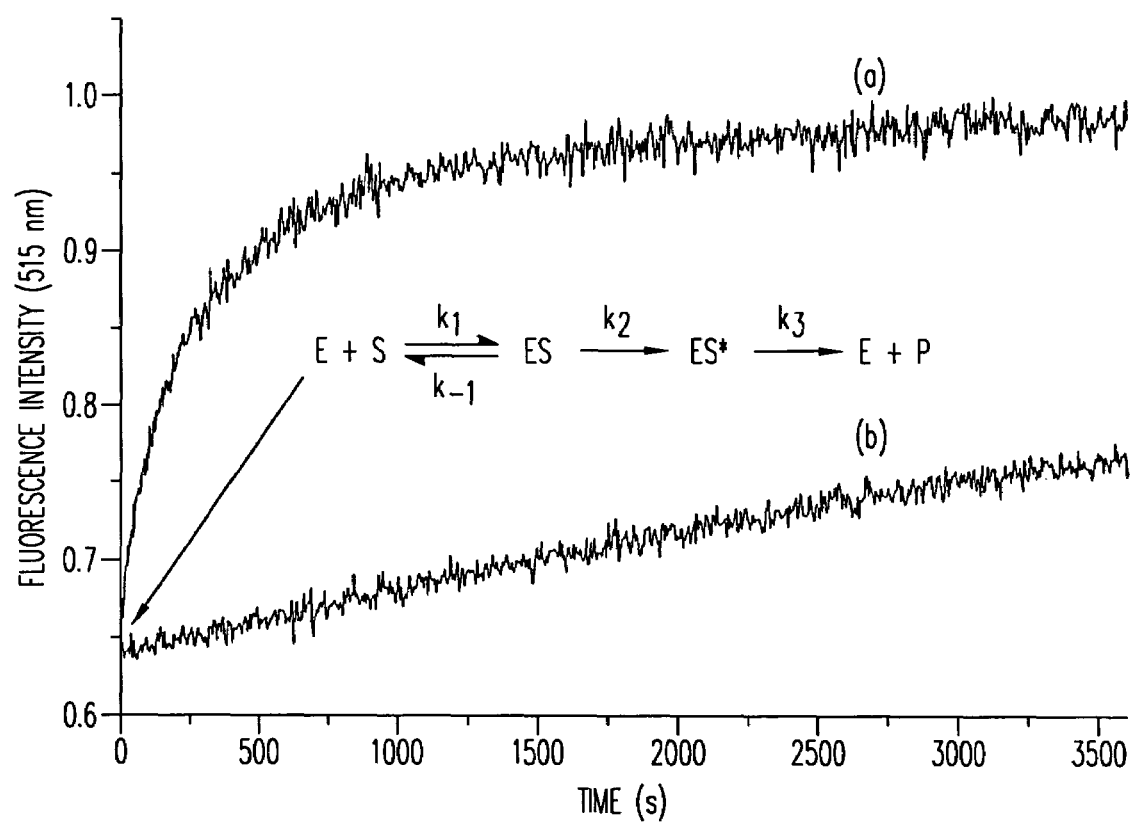
FIG. 14 shows the time-resolved fluorescence measurements of the E166Cf enzyme ($1.2\times10^{-7}$ M) at 515 nm in 50 mM phosphate buffer (pH 7.0) in the presence of $1.0\times10^{-4}$ M cefoxitin (a) and $1.0\times10^{-6}$ M cefoxitin (b). Excitation wavelength: 494 nm.
Figure 15:
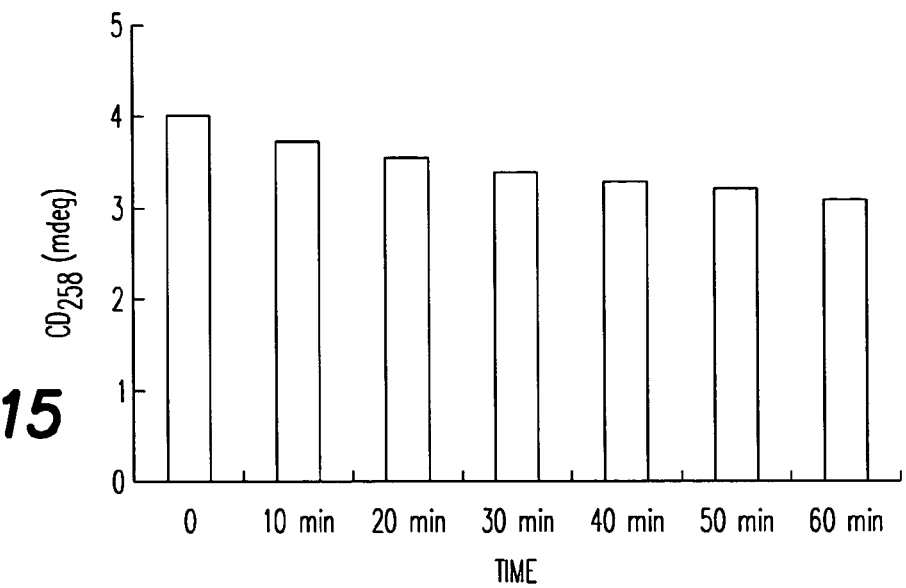
FIG. 15 shows the circular dichroism signals (258 nm) of cefuroxime in 50 mM phosphate buffer (pH 7.0) as a function of time in the presence of E166Cf enzyme ($1.2\times10^{-7}$ M)
Figure 16:
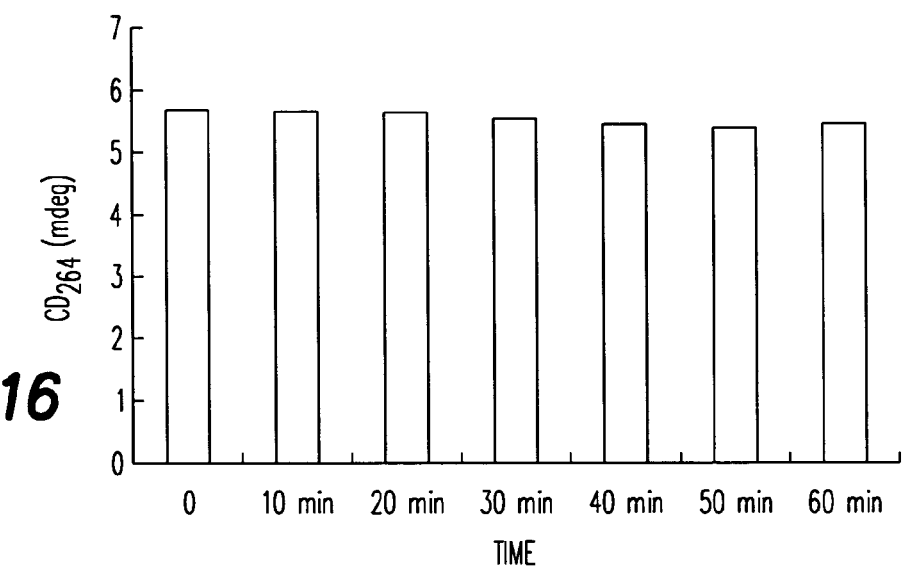
FIG. 16 shows the circular dichroism signals (264 nm) of cefoxitin in 50 mM phosphate buffer (pH 7.0) as a function of time in the presence of E166Cf enzyme ($1.2\times10^{-7}$ M)
Figure 17:
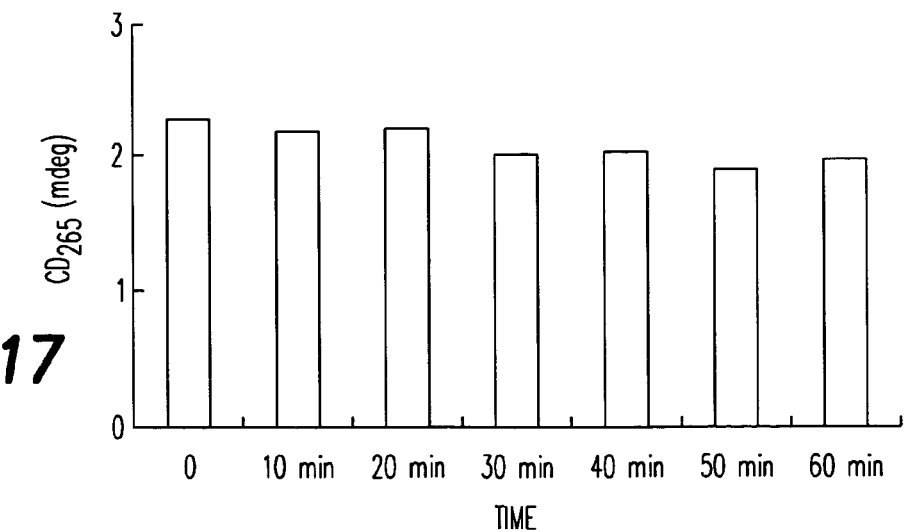
FIG. 17 shows the circular dichroism signals (265 nm) of moxalactam in 50 mM phosphate buffer (pH 7.0) as a function of time in the presence of E166Cf enzyme ($1.2\times10^{-7}$ M)

The absence of a declining fluorescence signal for cefuroxime, cefoxitin and moxalactam can be ascribed to the poor hydrolytic activities of the E166Cf enzyme towards these antibiotics (very low $k_2$ and/or $k_3$) (FIG. 14). As a result, the cephalosporin substrates stay in the active sites. To verify this, the activities of the labeled enzyme with cefuroxime, cefoxitin and moxalactam as substrates were monitored by circular dichroism (CD) spectropolarimetry. The principle of this assay is that β-lactam antibiotics, due to the asymmetric property of their fused ring systems, exhibit strong CD signals, but will become CD inactive when they are hydrolyzed by β-lactamase. Therefore, by measuring the CD signals of cefuroxime, cefoxitin and moxalactam ($1.0 \times 10^{-4}$ M) at 258, 264 and 265 nm respectively as a function of time in the presence of E166Cf enzyme ($1.2 \times 10^{-7}$ M), the hydrolytic activities of the labeled enzyme towards these antibiotics can be monitored. As shown in FIGS. 15 to 17, no significant changes in the CD signals appear after incubating the E166Cf enzymes with the cephalosporin antibiotics for one hour. This indicates that cefuroxime, cefoxitin and moxalactam are resistant to the hydrolytic activity of the labeled enzyme.

Fluorescence Measurements of the E166Cf Enzyme in the Presence of β-Lactamase Inhibitors Time-resolved fluorescence measurements of the E166Cf enzyme in the presence of sulbactam and clavulanate were performed on a Perkin Elmer LS50B spectrofluorometer. The excitation and emission wavelengths were set at 494 and 515 nm respectively. Both excitation and emission slit widths were set at 5 nm. All fluorescence measurements were performed at room temperature.

Figure 18:
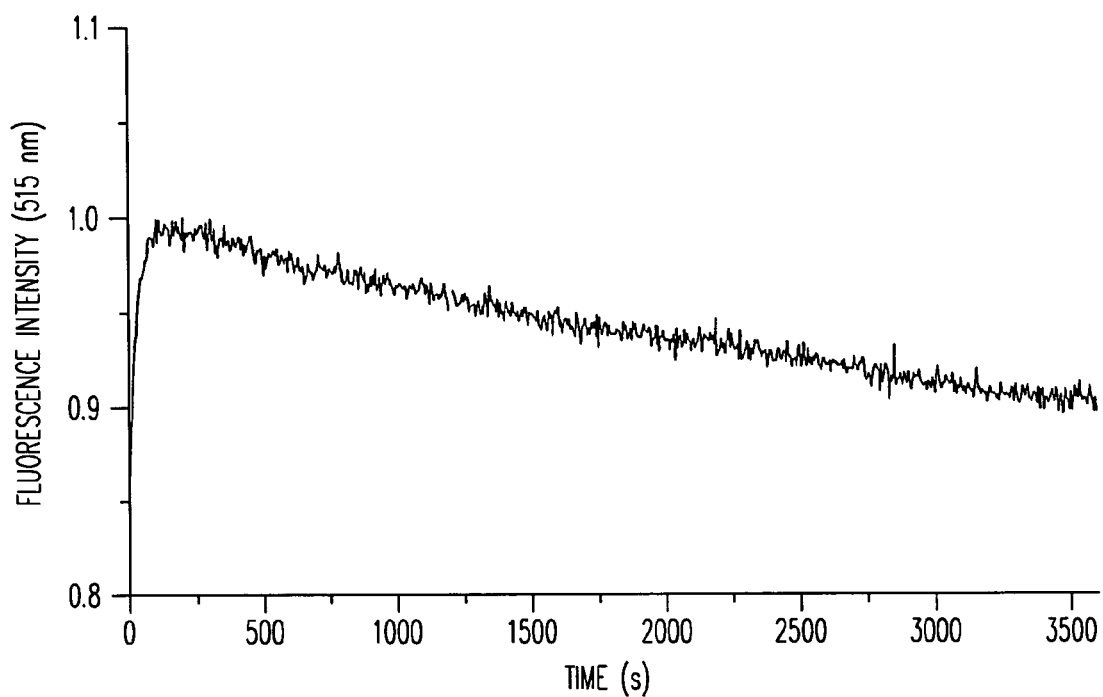
FIG. 18 shows the time-resolved fluorescence measurements of the E166Cf enzyme ($1.2\times10^{-7}$ M) at 515 nm in 50 mM phosphate buffer (pH 7.0) with $1.0\times10^{-4}$ M sulbactam as substrate. Excitation wavelength: 494 nm.
Figure 19:
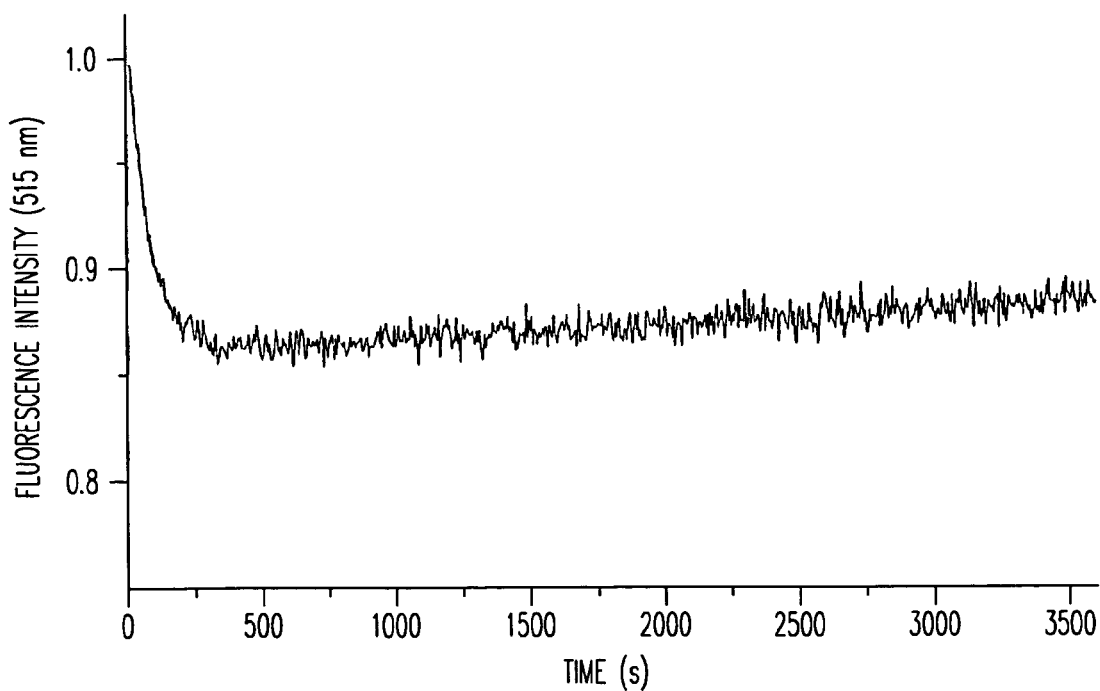
FIG. 19 shows the time-resolved fluorescence measurements of the E166Cf enzyme ($1.2\times10^{-7}$ M) at 515 nm in 50 mM phosphate buffer (pH 7.0) with $1.0\times10^{-3}$ M clavulanate as substrate. Excitation wavelength: 494 nm.

The fluorescence signals of the labeled enzyme ($1.2 \times 10^{-7}$ M) obtained with sulbactam ($1.0 \times 10^{-4}$ M) and clavulanate ($1.0 \times 10^{-3}$ M) in 50 mM phosphate buffer (pH 7.0) are entirely different (FIGS. 18 and 19). For sulbactam, the fluorescence intensity increases rapidly at the initial stage and then declines slowly. For clavulanate, the addition of substrate causes an instantaneous increase in fluorescence signal which declines rapidly within 200 s and then levels off to a plateau. These results indicate that the E166Cf enzyme can be used to detect β-lactamase inhibitors.

Detection of β-Lactam Antibiotics in Milk

Figure 20A:
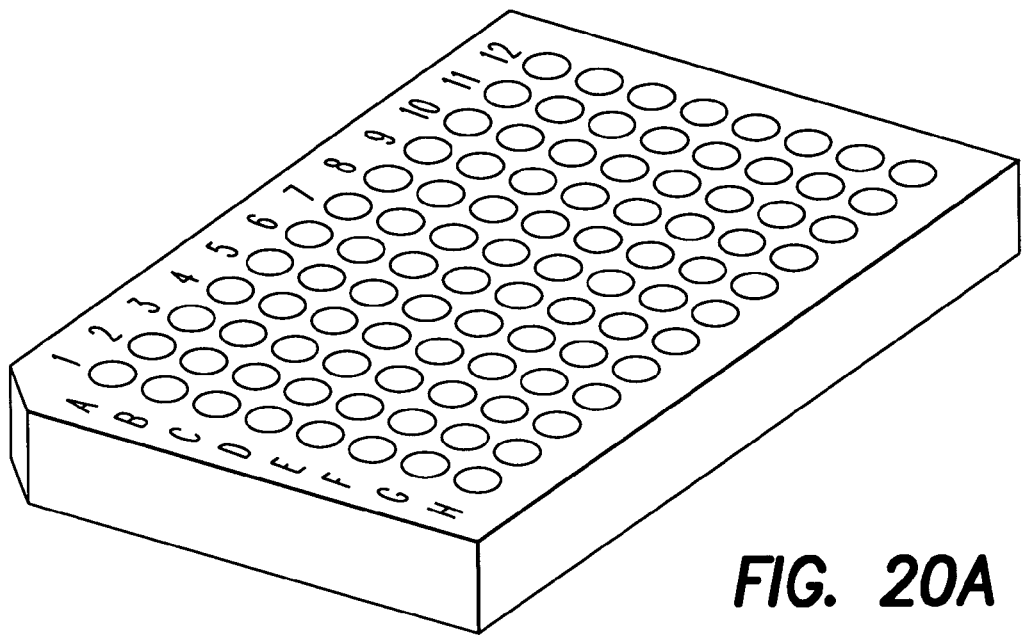
FIG. 20 shows the (A) A 96-well microtiter plate (Corning Costar) and (B) the schematic diagram of the set-up used in the detection of β-lactam antibiotics in milk and in drug screening experiments.
Figure 20B:
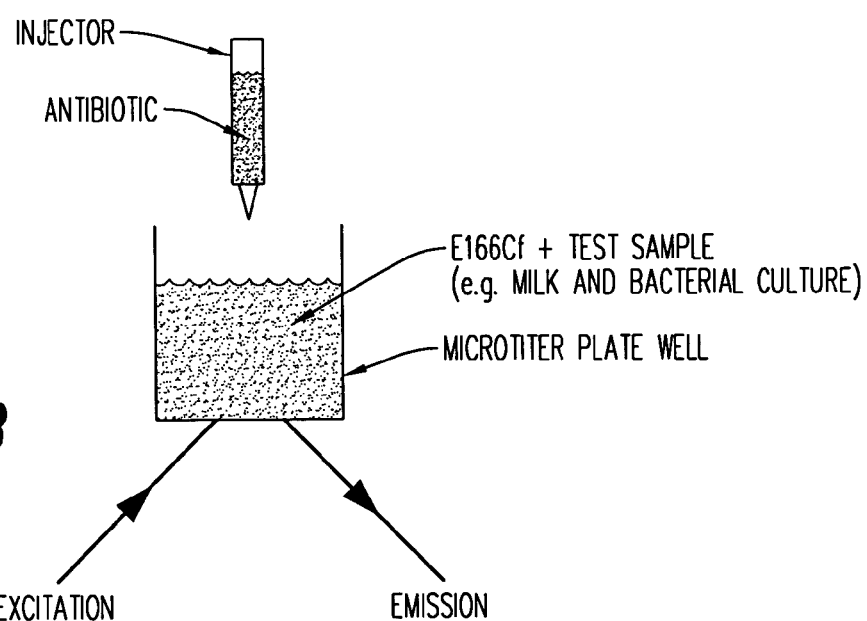

Fluorescence measurements of the E166Cf enzyme in milk in the presence of penicillin G and ampicillin were performed on a FLUOstar microplate reader (BMG Labtechnologies) equipped with two sample injectors. Excitation and emission filters of 485 and 520 nm respectively were used. Milk (pasteurized and homogenized, Nestle Dairy Farm) was purchased at a local supermarket. The labeled enzyme was mixed with the milk sample in a 96-well microtiter plate (Corning Costar). The antibiotics were then added to the mixtures by the injectors. The experimental set-up is shown in FIG. 20.

Figure 21:
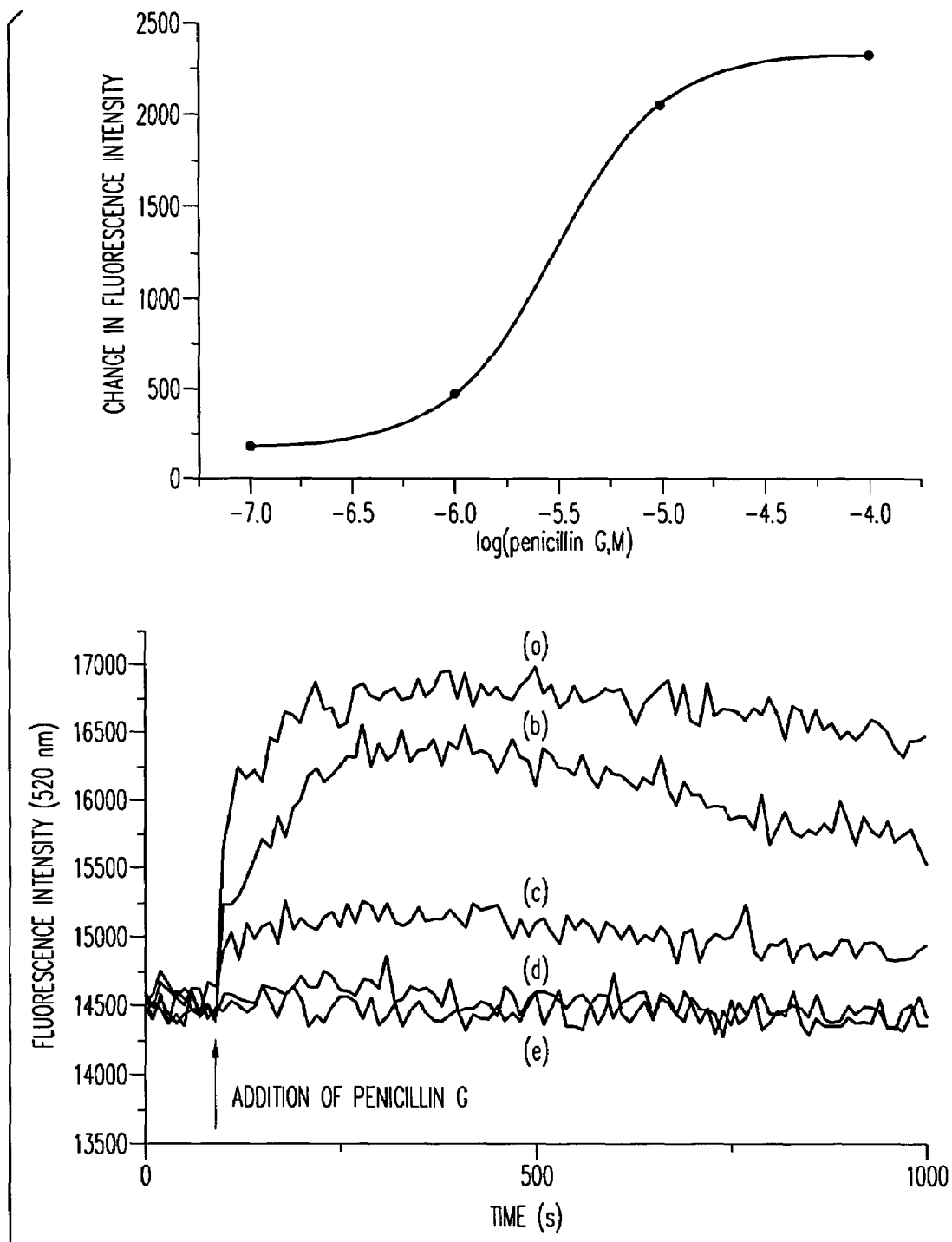
FIG. 21 shows the time-resolved fluorescence measurements of the E166Cf enzyme ($1.2\times10^{-7}$ M) at 520 nm in untreated milk in the presence of $1.0\times10^{-4}$ M penicillin G (a), $1.0\times10^{-5}$ M penicillin G (b), $1.0\times10^{-6}$ M penicillin G (c), $1.0\times10^{-7}$ M penicillin G (d) and in the absence of penicillin G (e). Excitation wavelength: 485 nm. The inset shows the plot of the change in fluorescence intensity (at the peak maxima) versus log (penicillin G, M)
Figure 22:
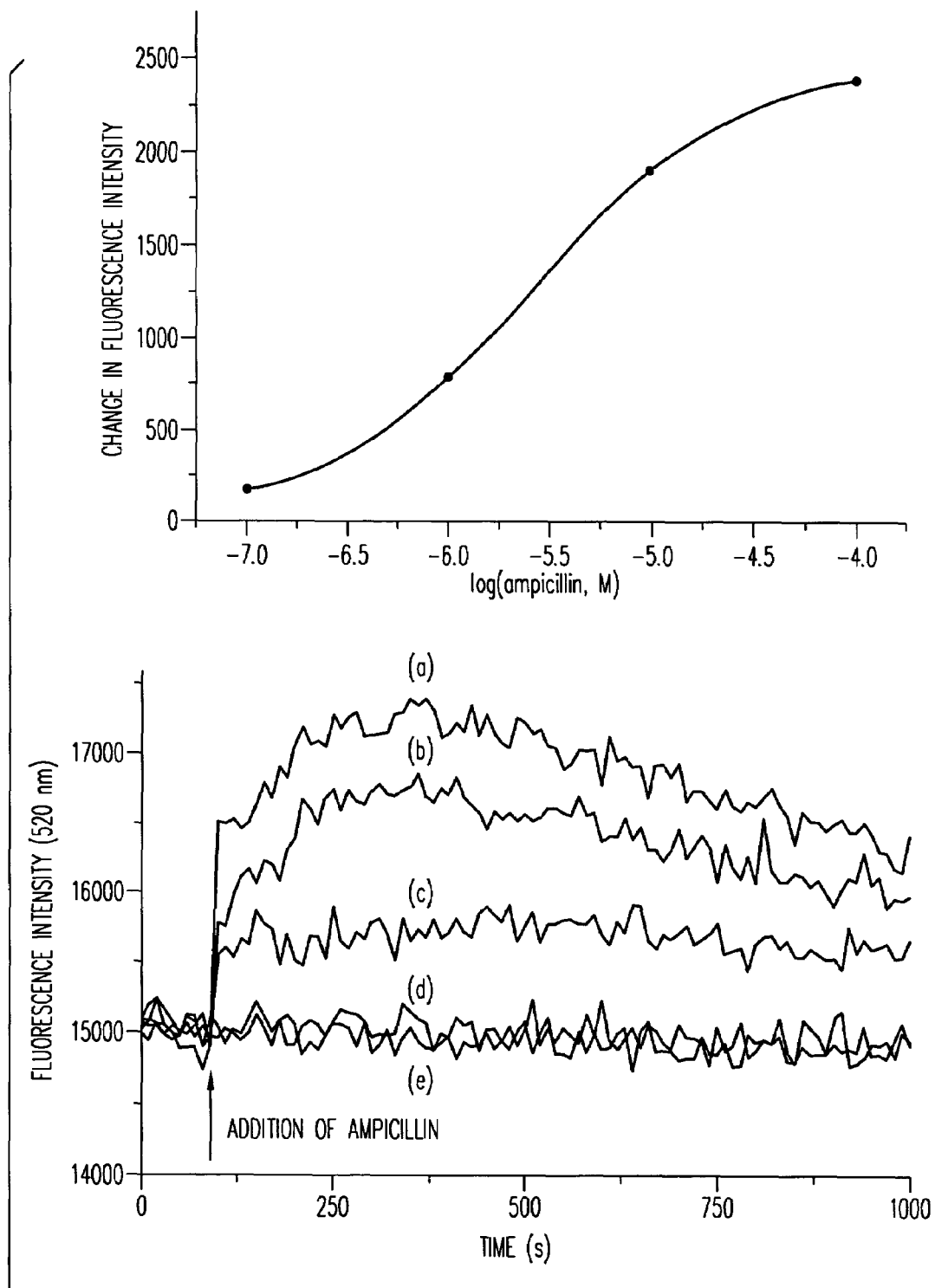
FIG. 22 shows the time-resolved fluorescence measurements of the E166Cf enzyme ($1.2\times10^{-7}$ M) at 520 nm in untreated milk in the presence of $1.0\times10^{-4}$ M ampicillin (a), $1.0\times10^{-5}$ M ampicillin (b), $1.0\times10^{-6}$ M ampicillin (c), $1.0\times10^{-7}$ M ampicillin (d) and in the absence of ampicillin (e). Excitation wavelength: 485 nm. The inset shows the plot of the change in fluorescence intensity (at the peak maxima) versus log (ampicillin, M)
Figure 23A:
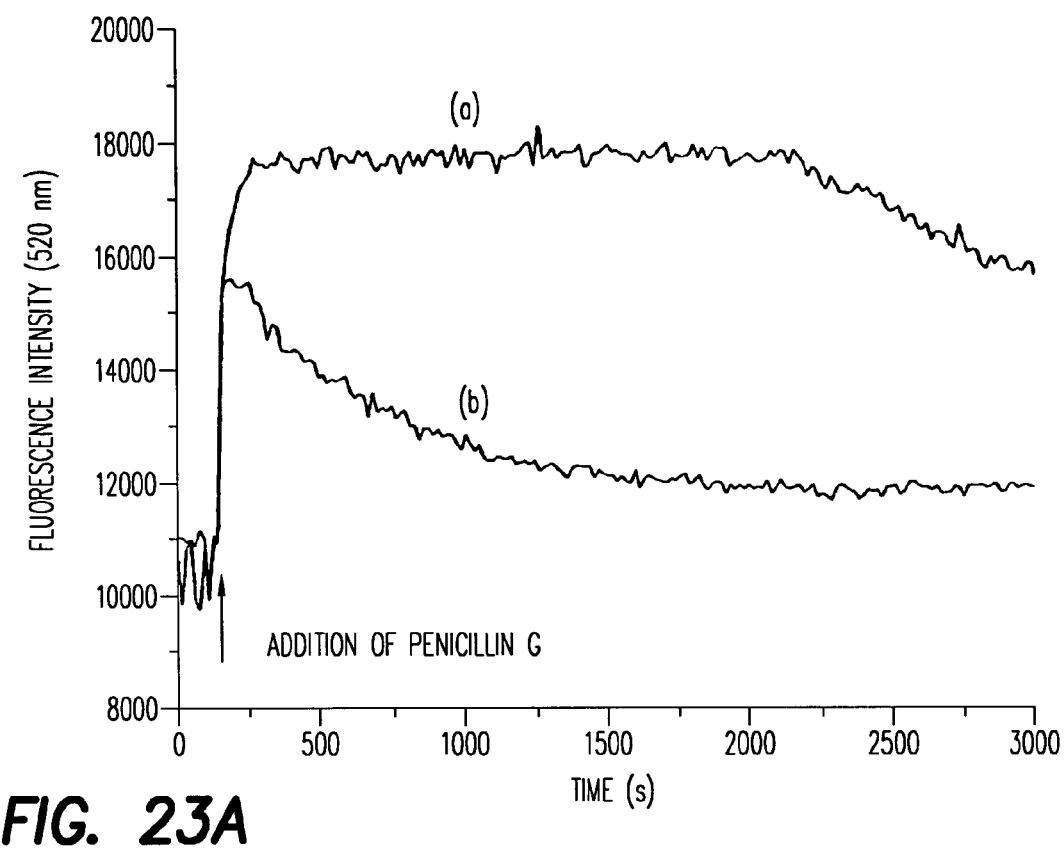
FIG. 23 shows the time-resolved fluorescence measurements of the E166Cf enzyme ($1.2\times10^{-7}$ M) in 50 mM phosphate buffer (pH 7.0) with (A) penicillin G ($1.0\times10^{-4}$ M), (B) penicillin V ($1.0\times10^{-4}$ M), (C) ampicillin ($1.0\times10^{-4}$ M), (D) cefuroxime ($1.0\times10^{-4}$ M), (E) cefoxitin ($1.0\times10^{-4}$ M) and (F) moxalactam ($1.0\times10^{-4}$ M) as substrates in the absence of β-lactamase II (a) and in the presence of β-lactamase II (b). Excitation wavelength: 485 nm.
Figure 23B:
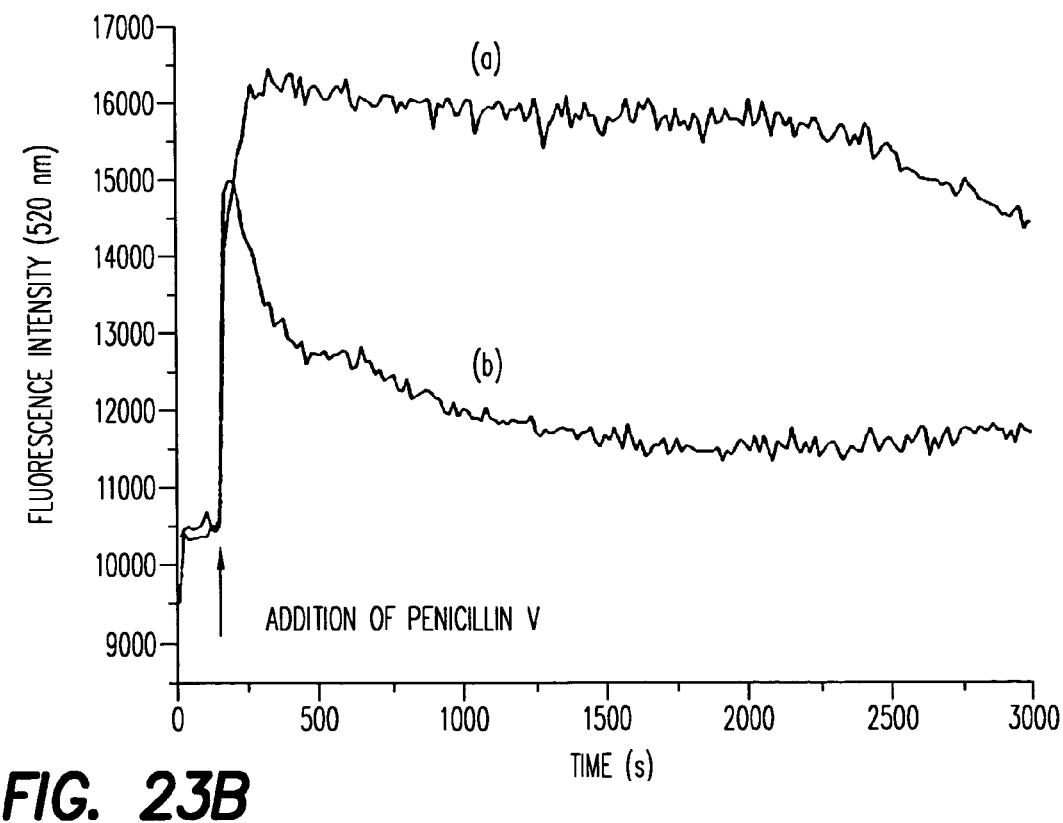
Figure 23C:
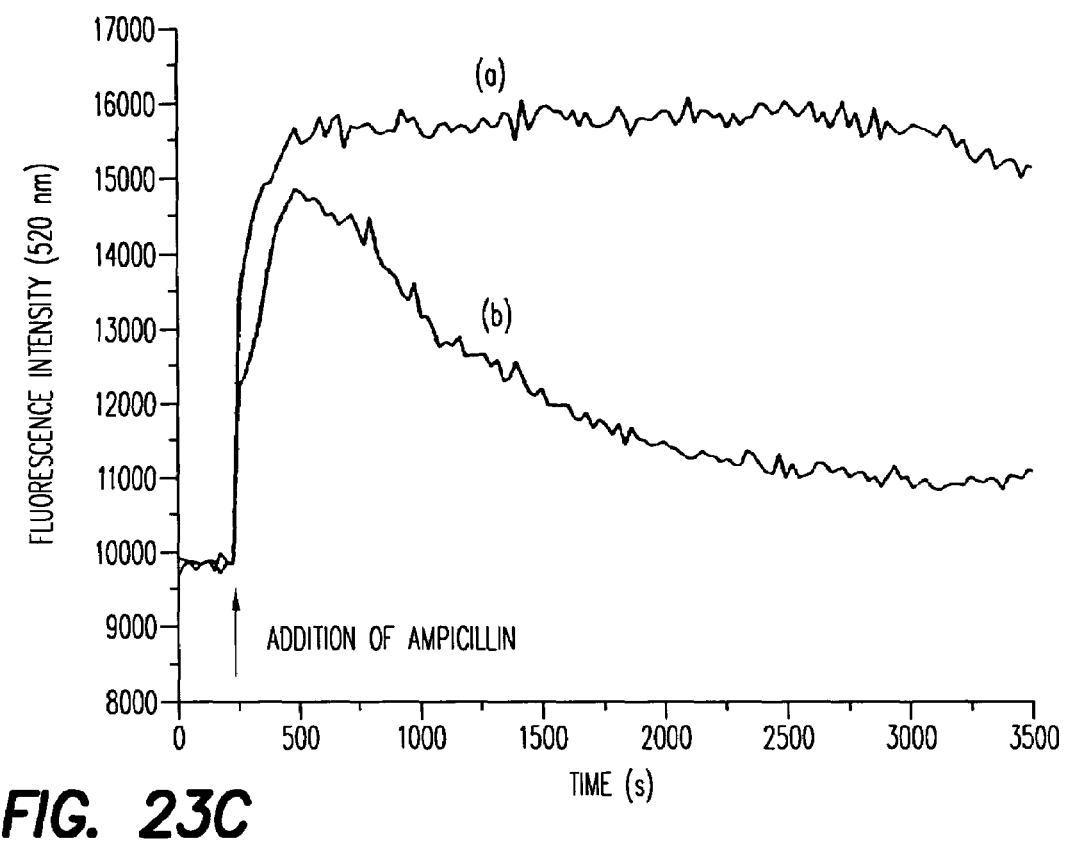
Figure 23D:
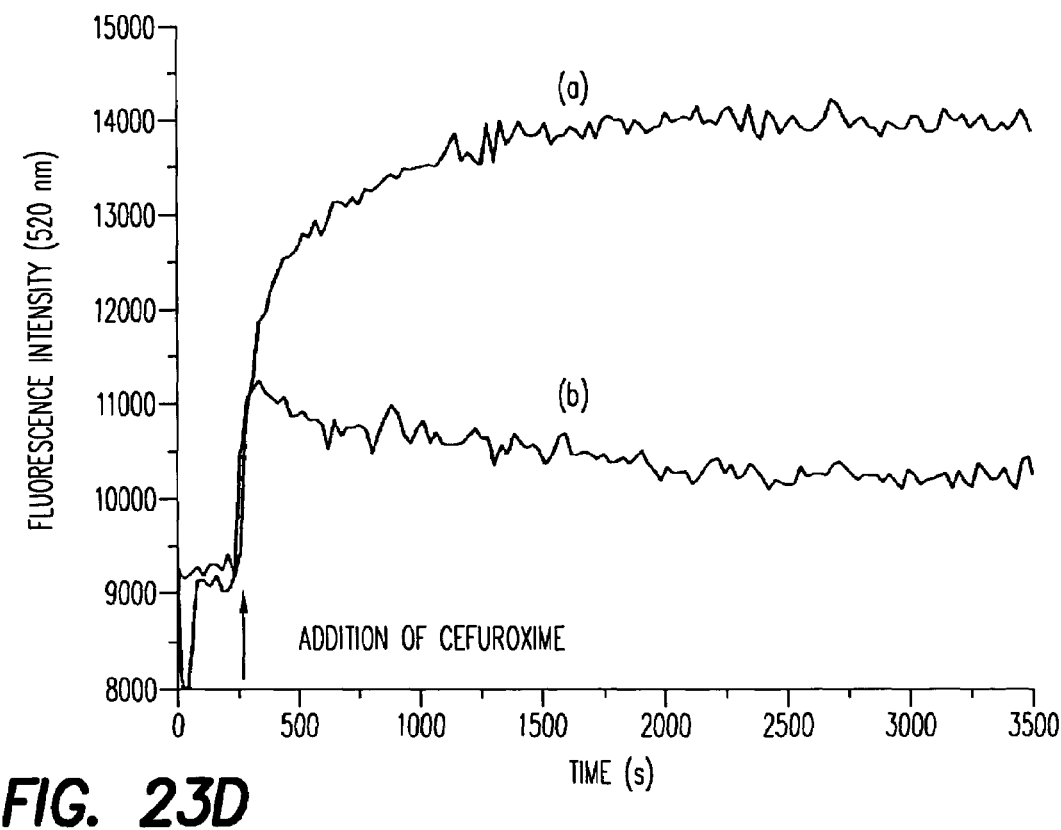
Figure 23E:
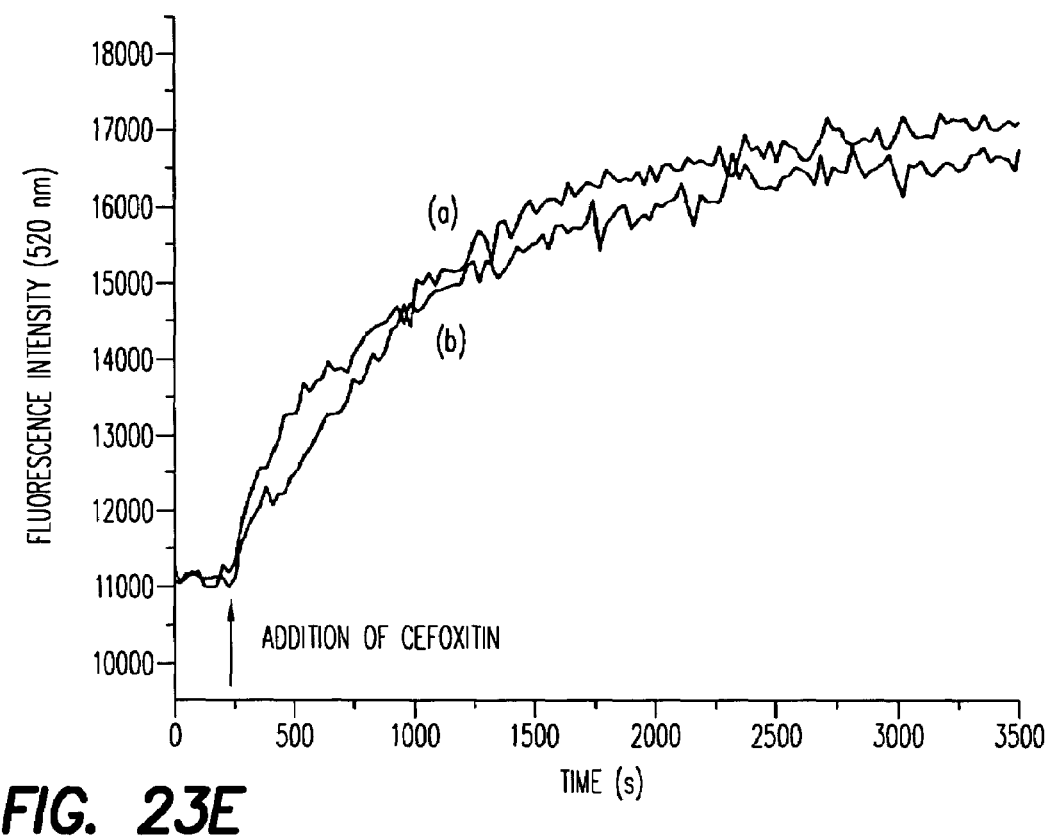
Figure 23F:
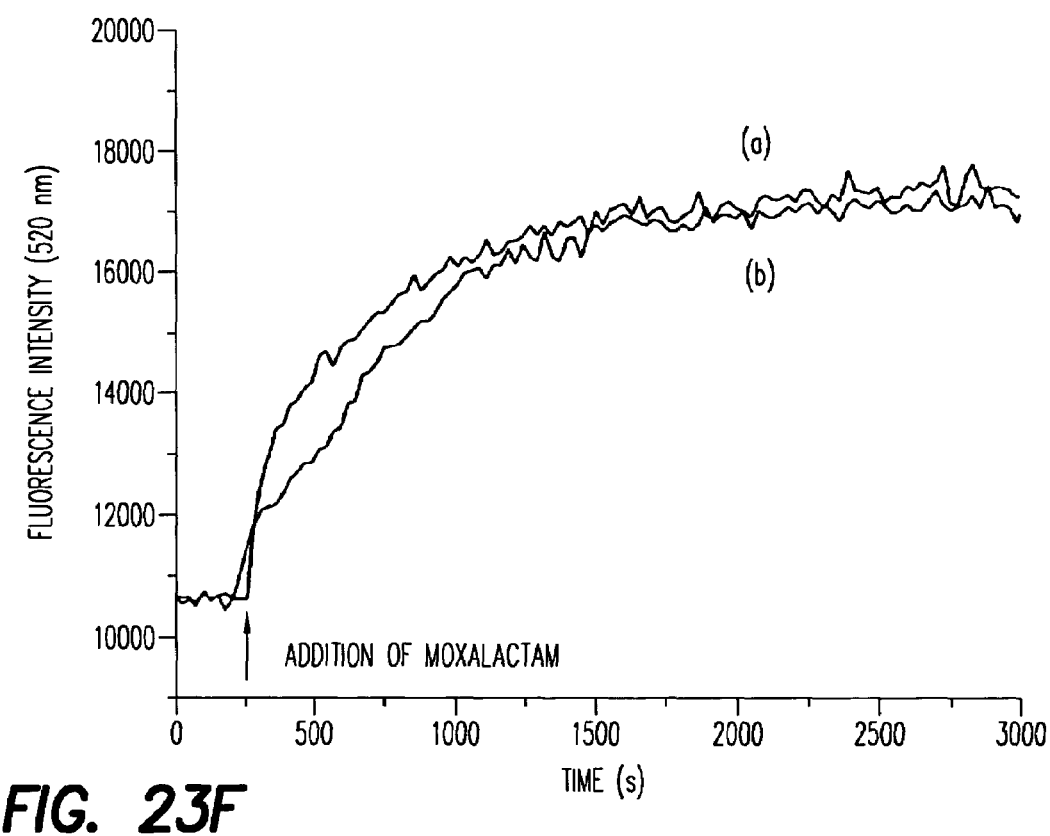
Figure 24A:
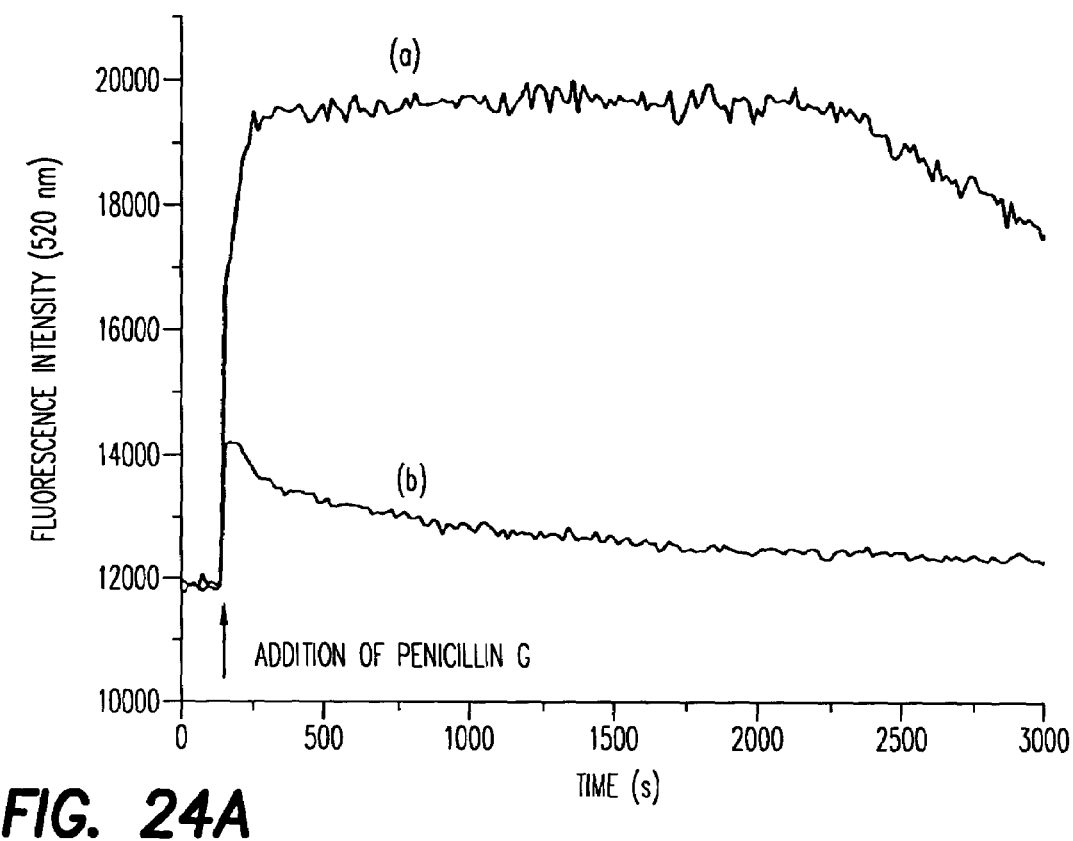
FIG. 24 shows the time-resolved fluorescence measurements of the E166Cf enzyme ($1.2\times10^{-7}$ M) in 50 mM phosphate buffer (pH 7.0) with (A) penicillin G ($1.0\times10^{-4}$ M), (B) penicillin V ($1.0\times10^{-4}$ M), (C) ampicillin ($1.0\times10^{-4}$ M), (D) cefuroxime ($1.0\times10^{-4}$ M), (E) cefoxitin ($1.0\times10^{-4}$ M) and (F) moxalactam ($1.0\times10^{-4}$ M) as substrates in the absence of penPC β-lactamase (a) and in the presence of penPC β-lactamase (b). Excitation wavelength: 485 nm.
Figure 24B:
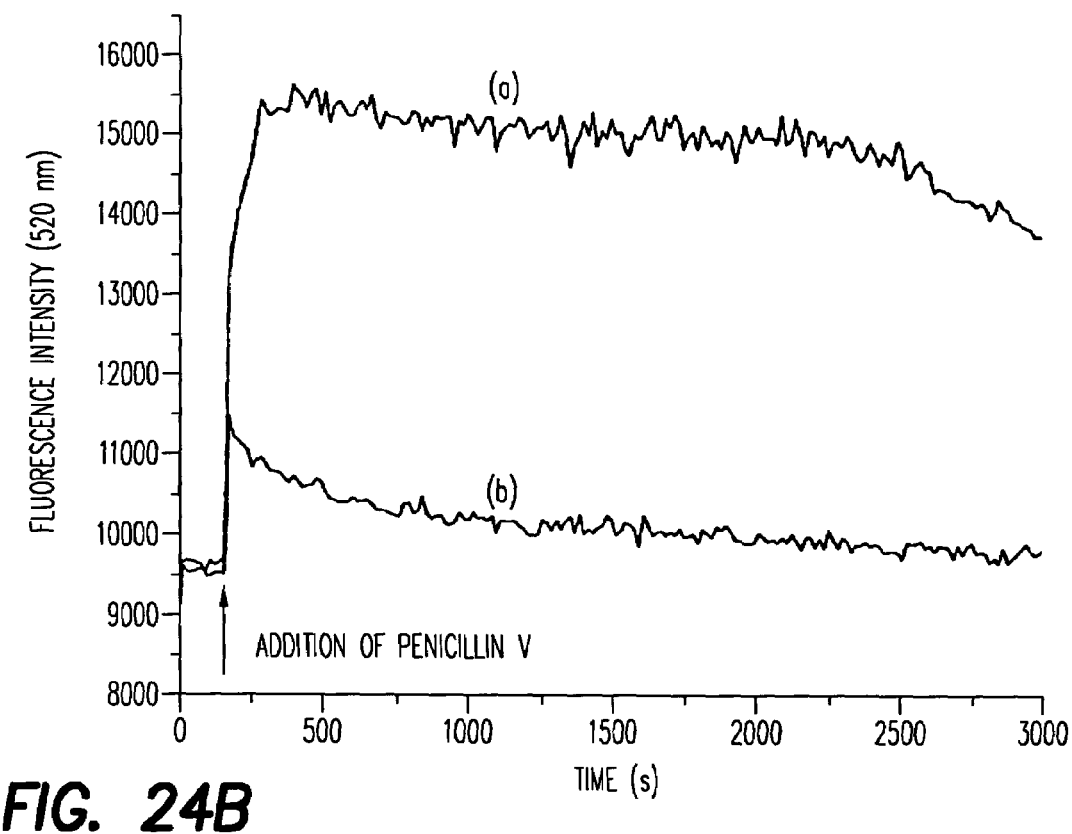
Figure 24C:
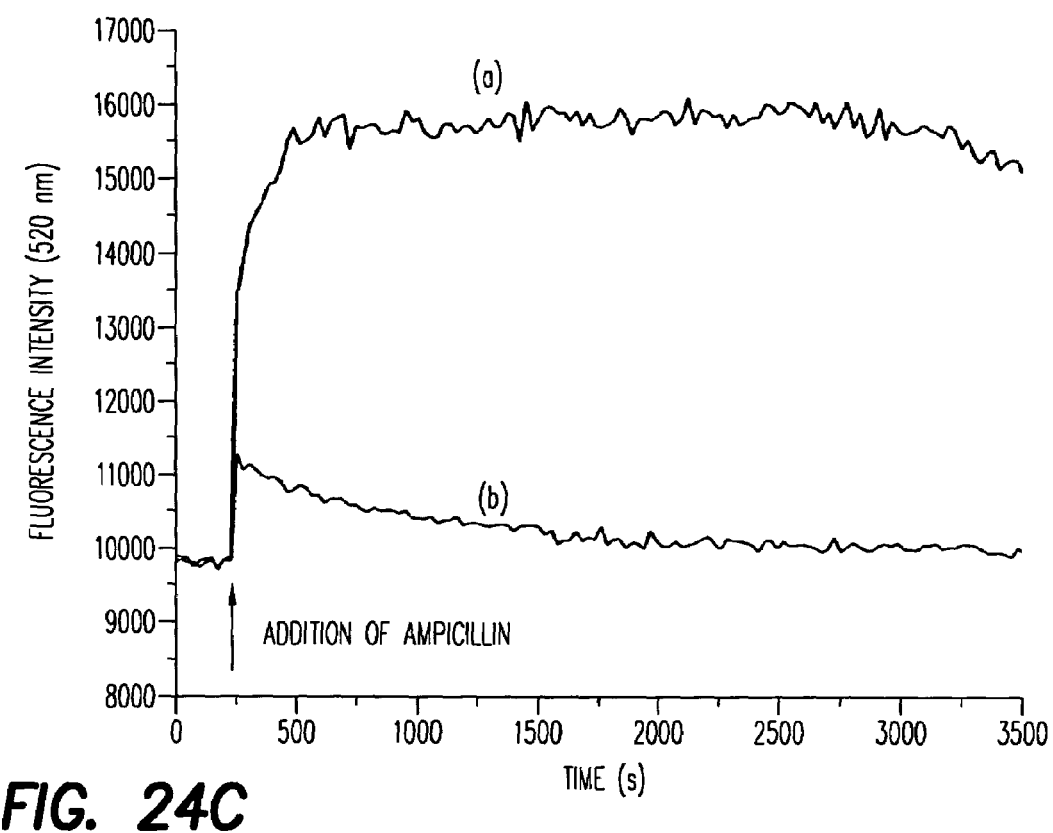
Figure 24D:
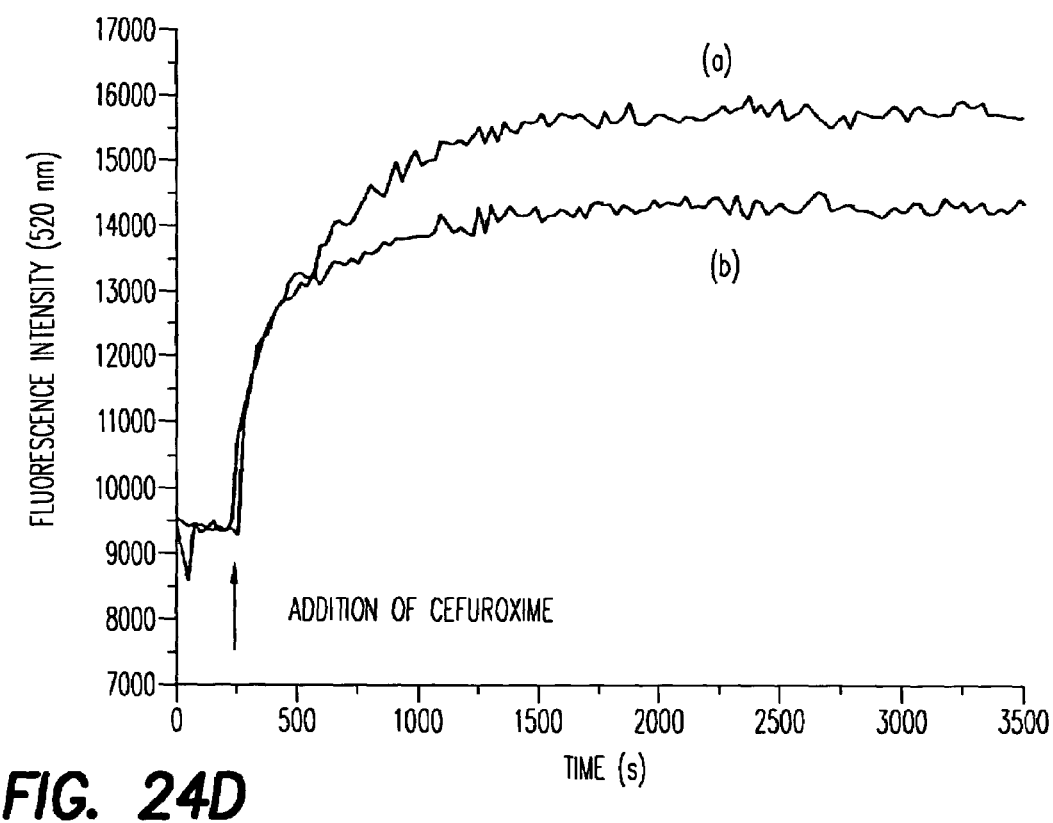
Figure 24E:
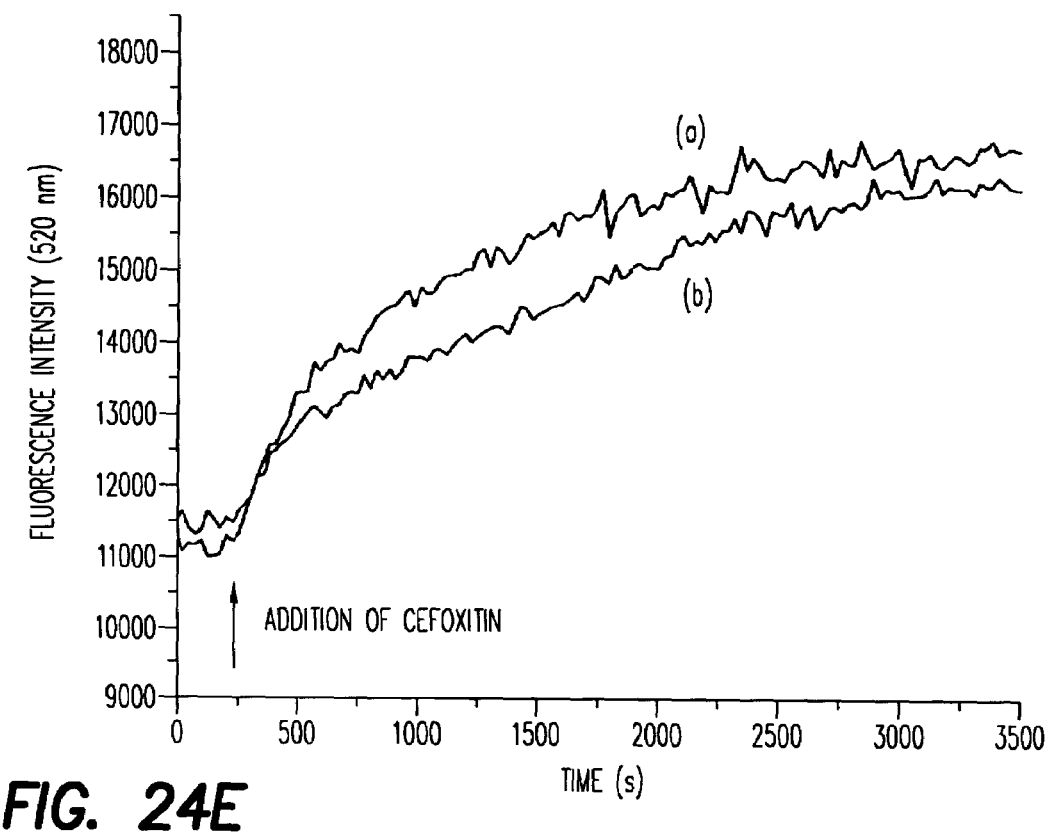
Figure 24F:
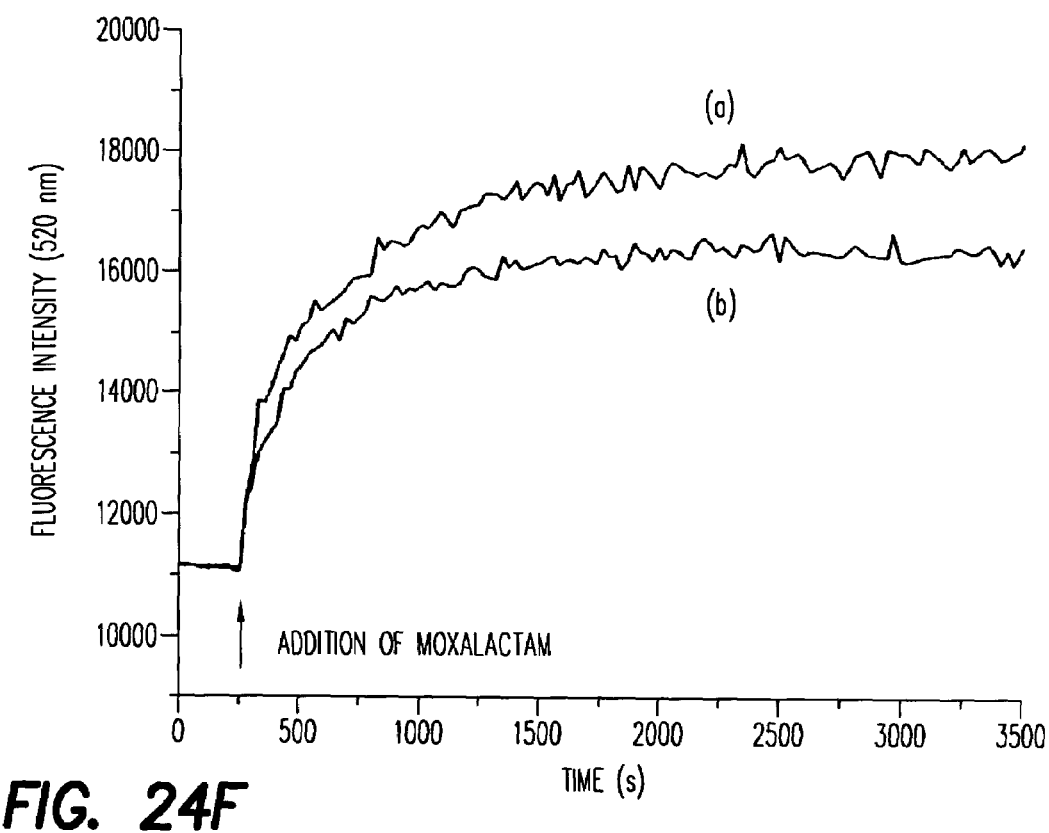
Figure 25A:
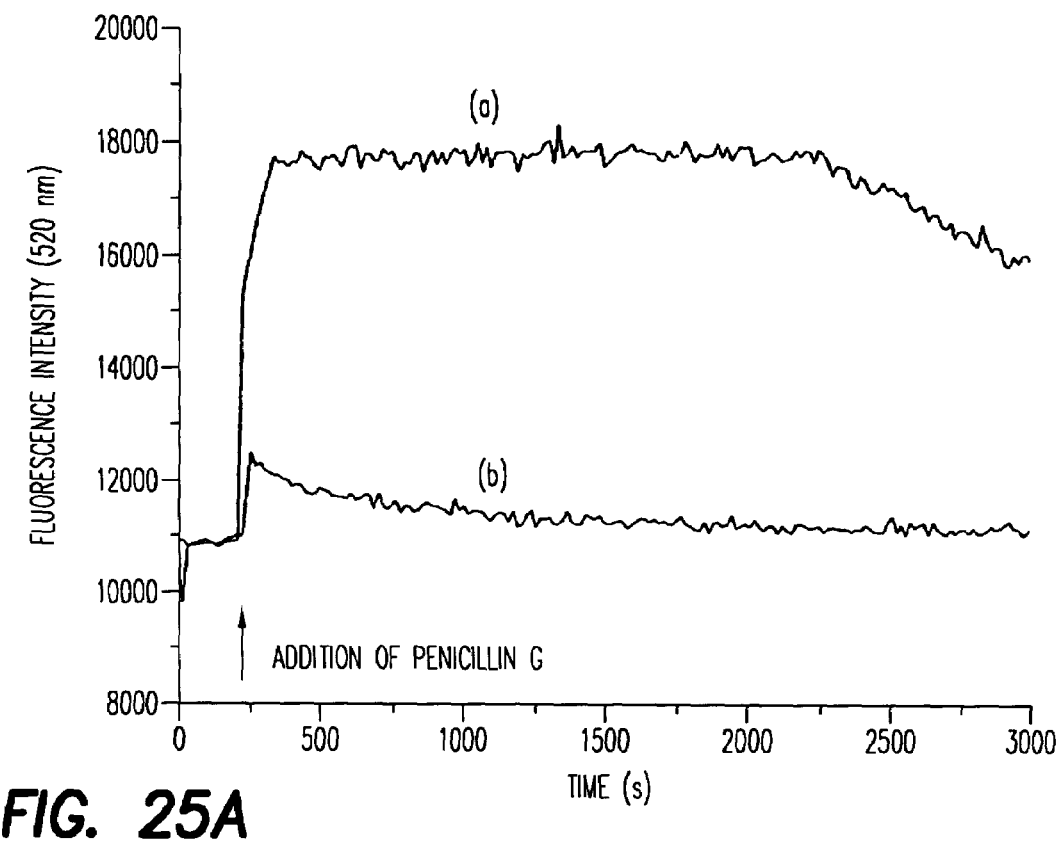
FIG. 25 shows the time-resolved fluorescence measurements of the E166Cf enzyme ($1.2\times10^{-7}$ M) in 50 mM phosphate buffer (pH 7.0) with (A) penicillin G ($1.0\times10^{-4}$ M), (B) penicillin V ($1.0\times10^{-4}$ M), (C) ampicillin ($1.0\times10^{-4}$ M), (D) cefuroxime ($1.0\times10^{-4}$ M), (E) cefoxitin ($1.0\times10^{-4}$ M) and (F) moxalactam ($1.0\times10^{-4}$ M) as substrates in the absence of penP β-lactamase (a) and in the presence of penP β-lactamase (b). Excitation wavelength: 485 nm.
Figure 25B:
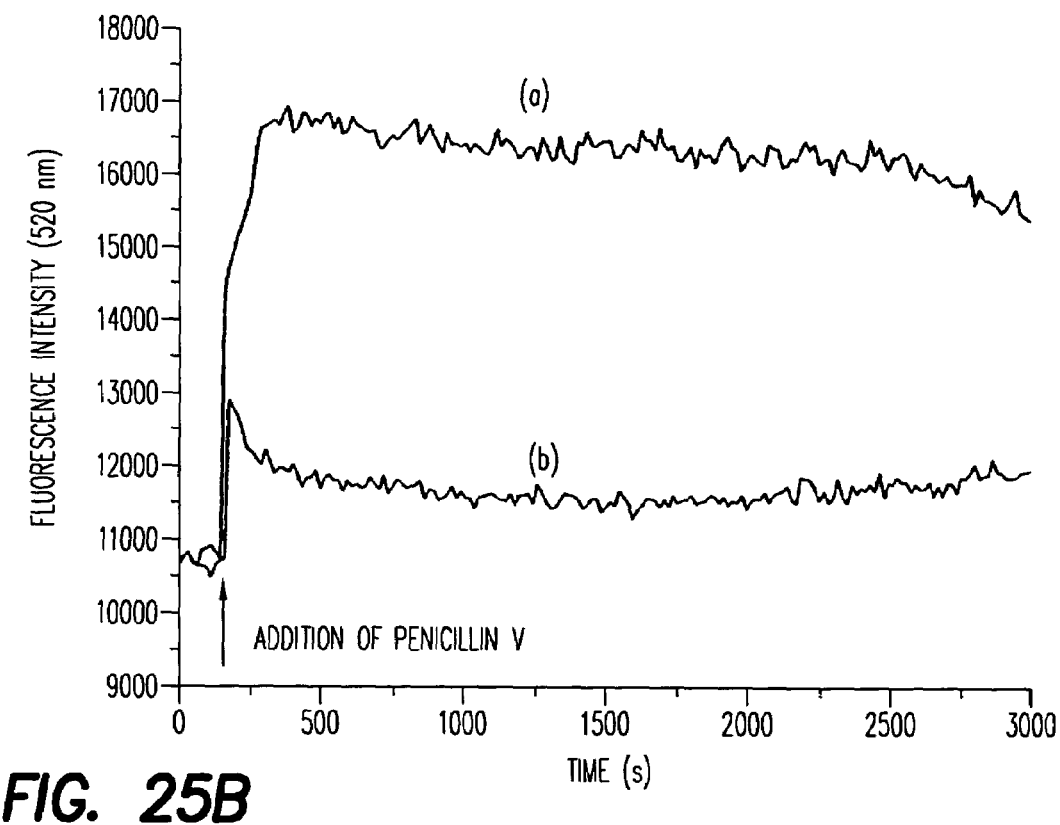
Figure 25C:
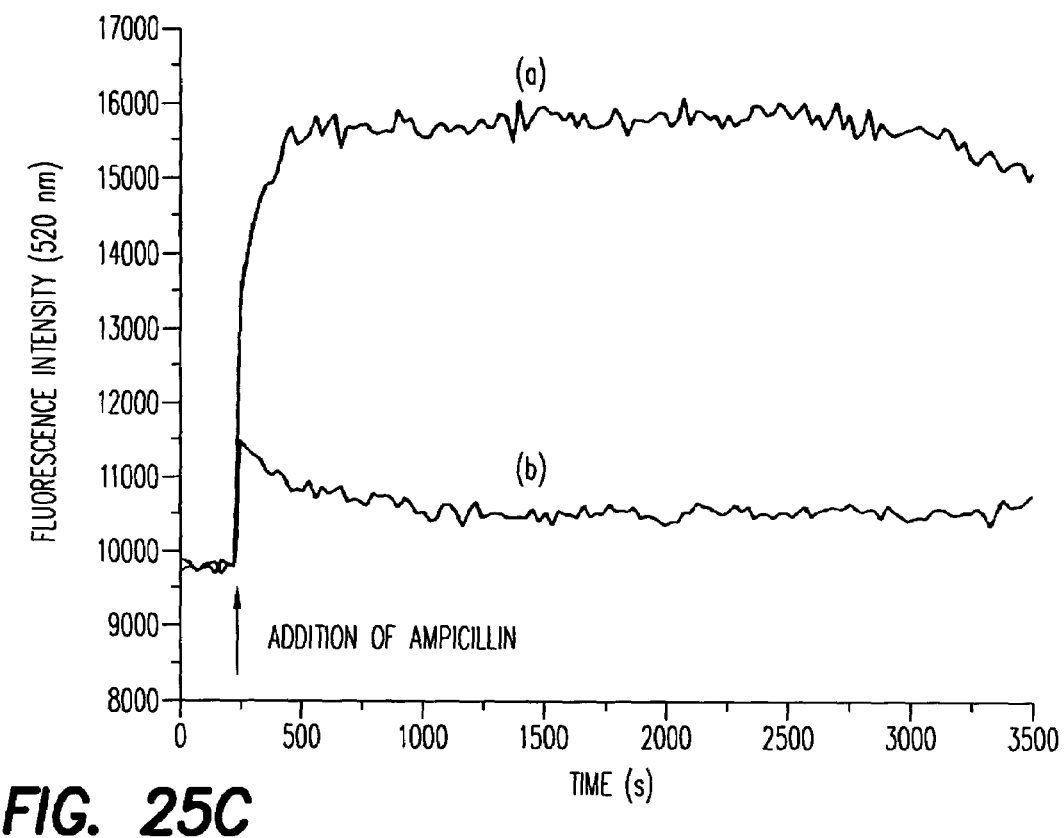
Figure 25D:
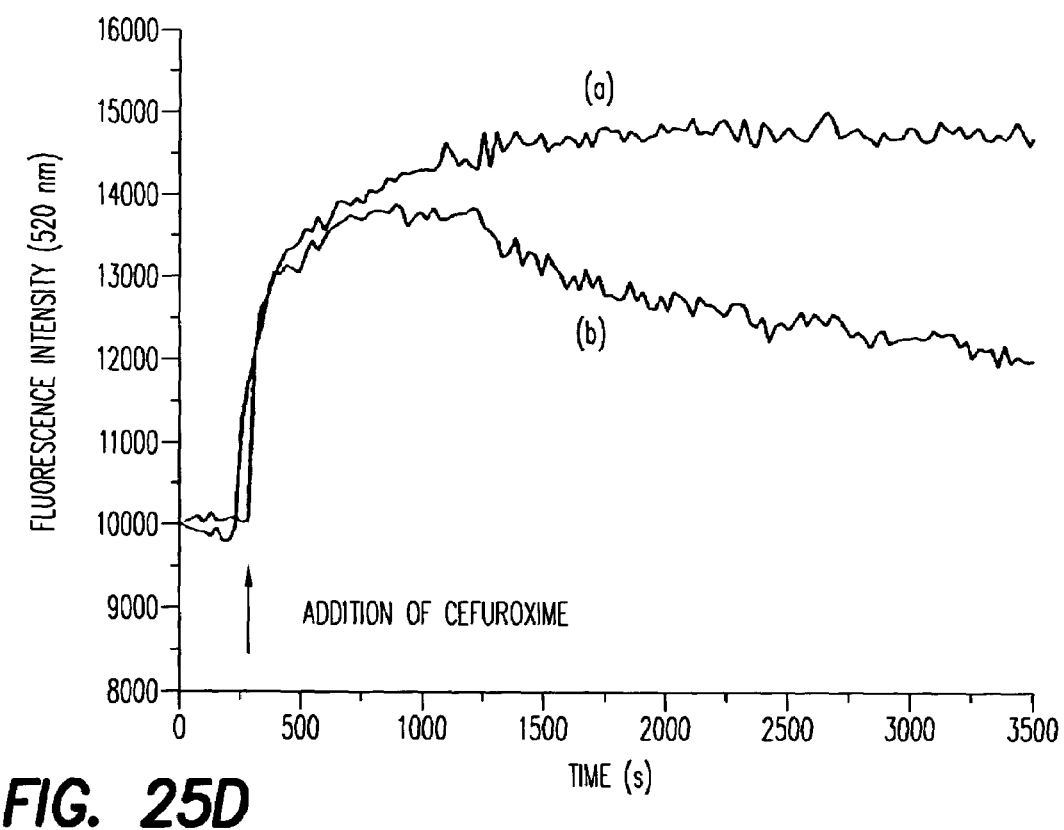
Figure 25E:
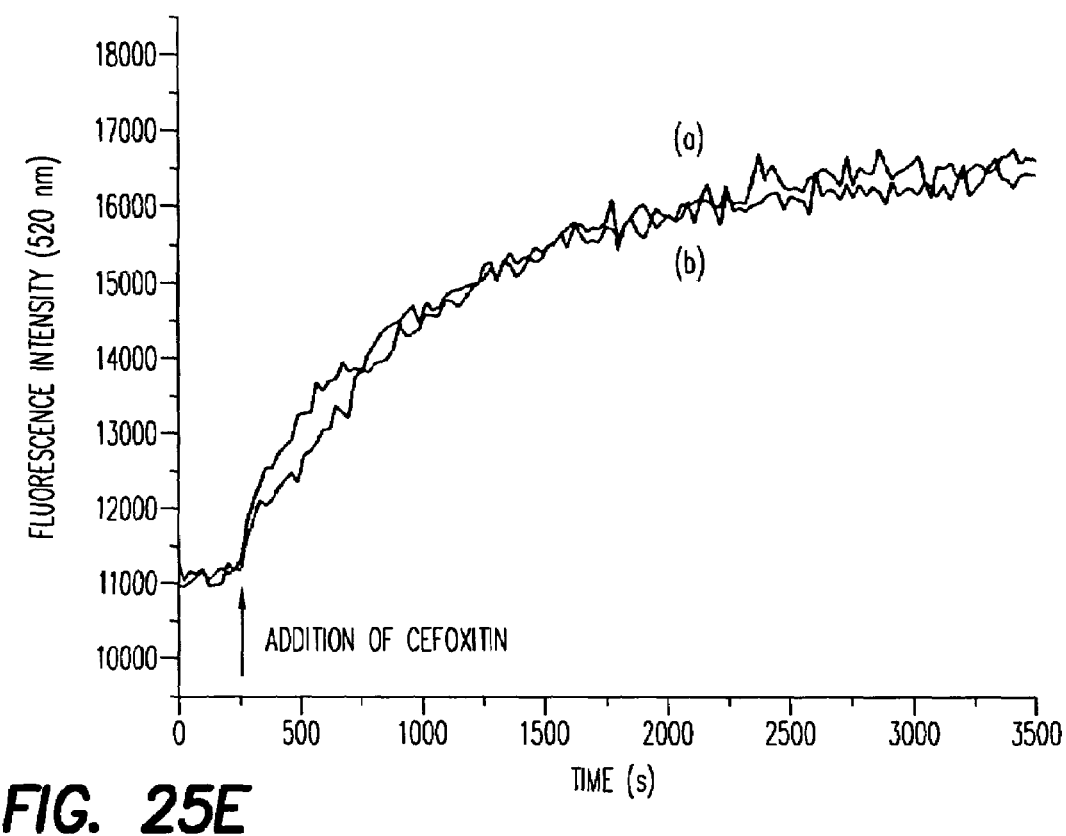
Figure 25F:
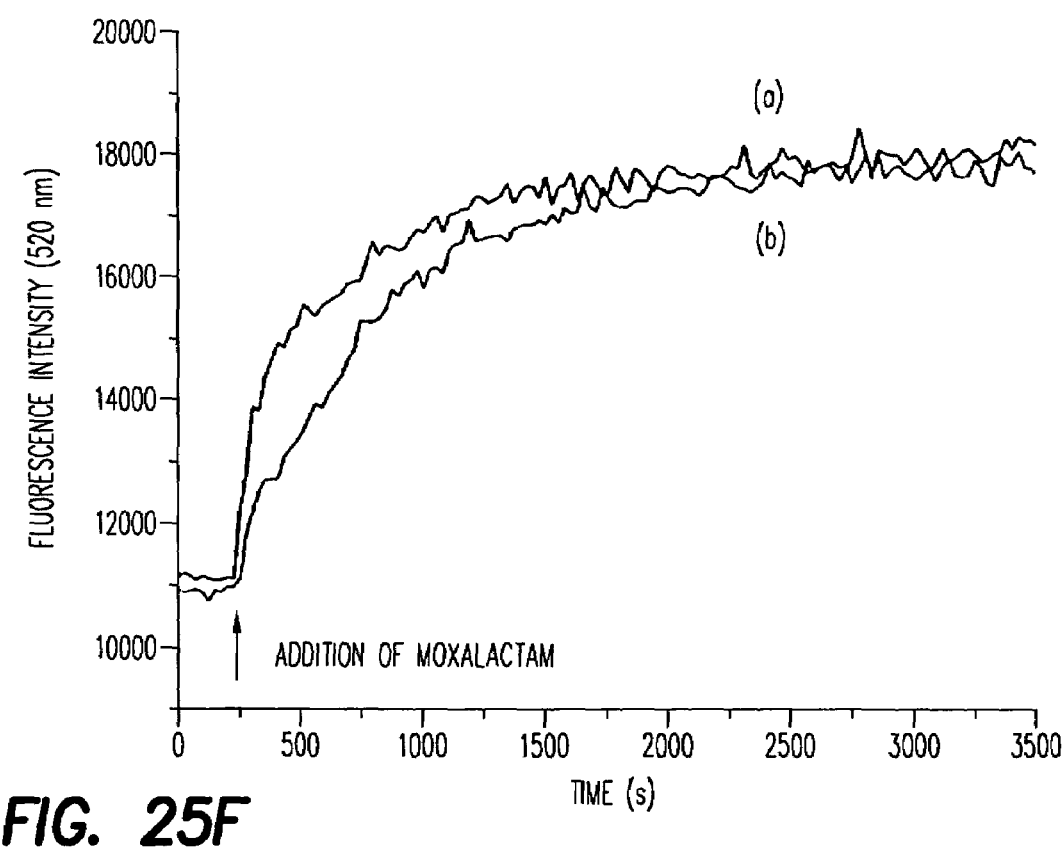
Figure 26A:
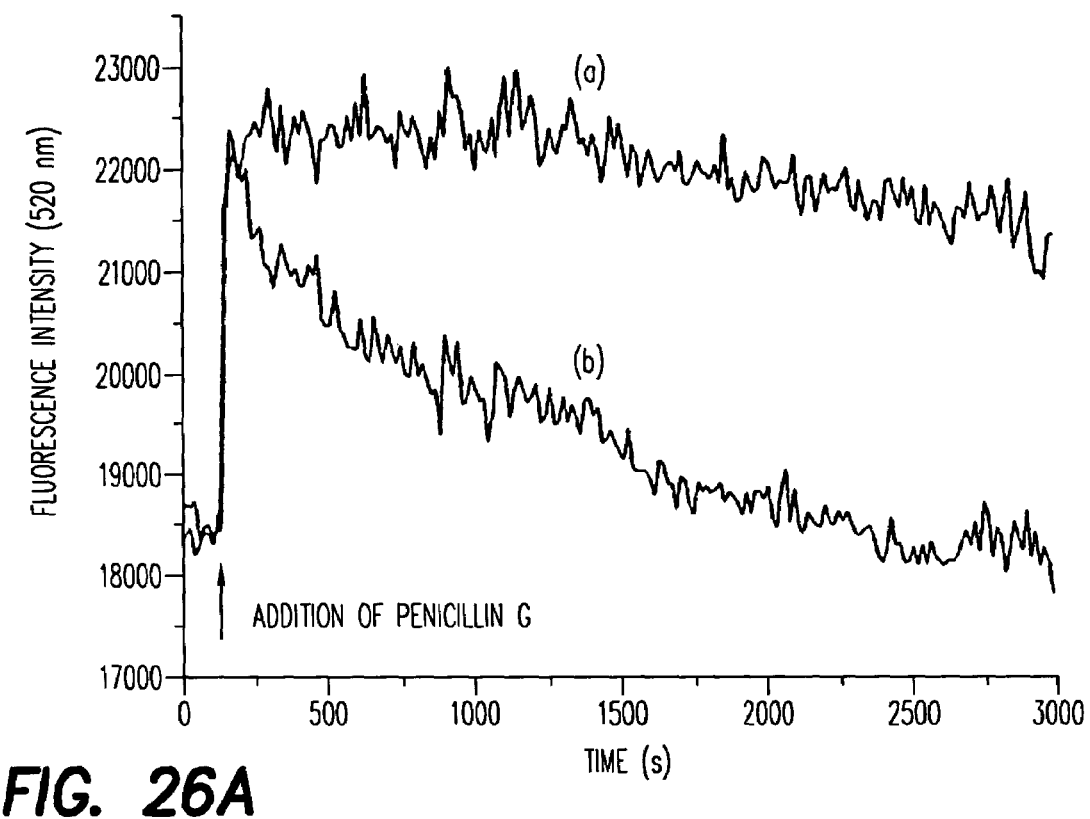
FIG. 26 shows the time-resolved fluorescence measurements of the E166Cf enzyme ($1.2\times10^{-7}$ M) in 50 mM phosphate buffer (pH 7.0) with (A) penicillin G ($1.0\times10^{-4}$ M), (B) penicillin V ($1.0\times10^{-4}$ M), (C) ampicillin ($1.0\times10^{-4}$ M), (D) cefuroxime ($1.0\times10^{-4}$ M), (E) cefoxitin ($1.0\times10^{-4}$ M) and (F) moxalactam ($1.0\times10^{-4}$ M) as substrates in the absence of TEM-1 β-lactamase (a) and in the presence of TEM-1 β-lactamase (b). Excitation wavelength: 485 nm.
Figure 26B:
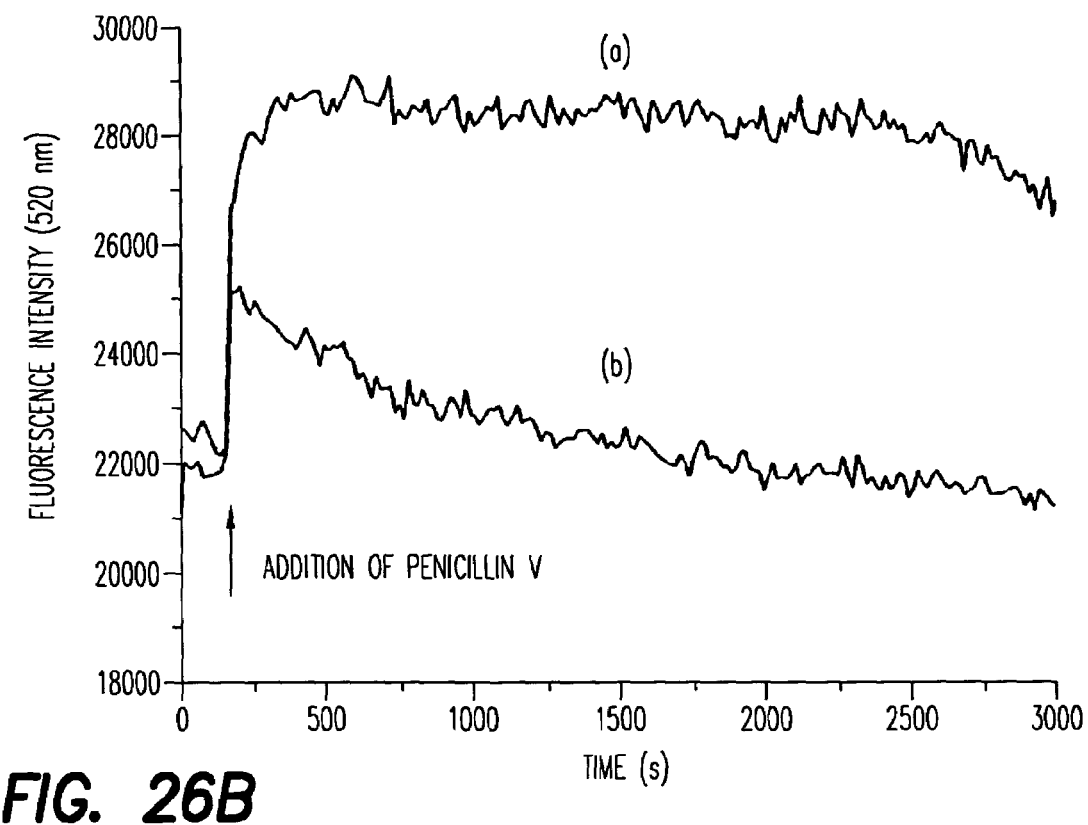
Figure 26C:
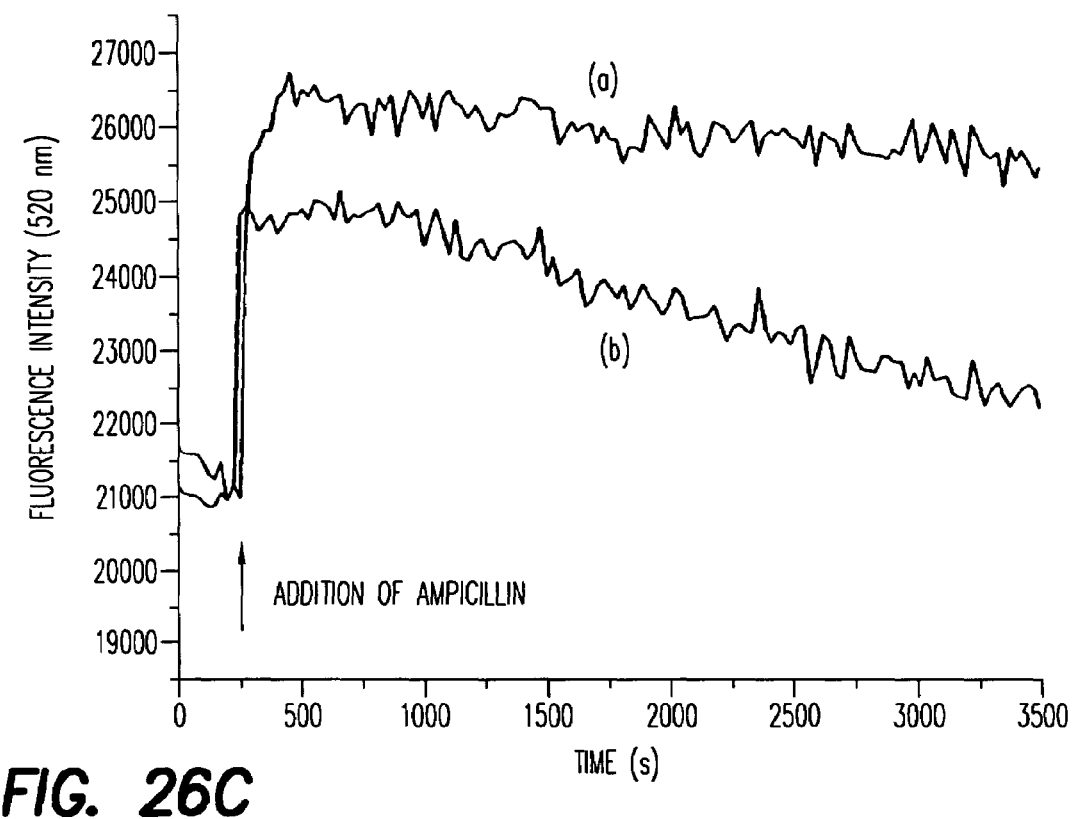
Figure 26D:
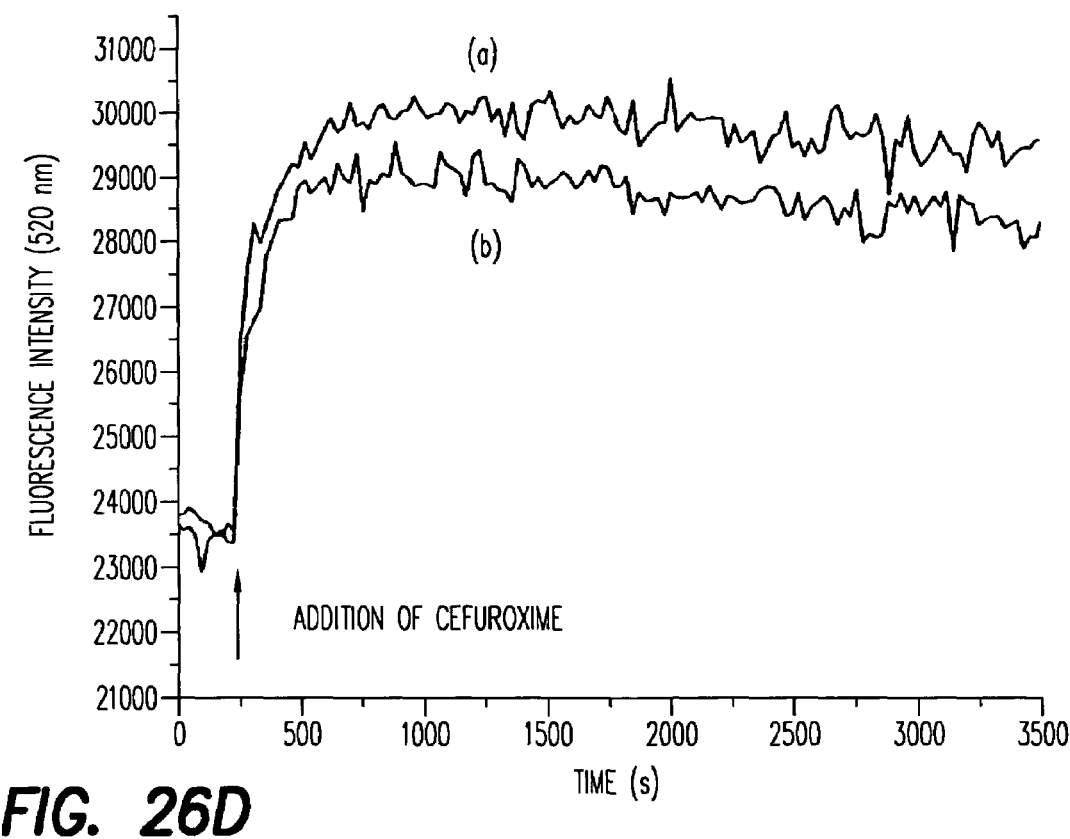
Figure 26E:
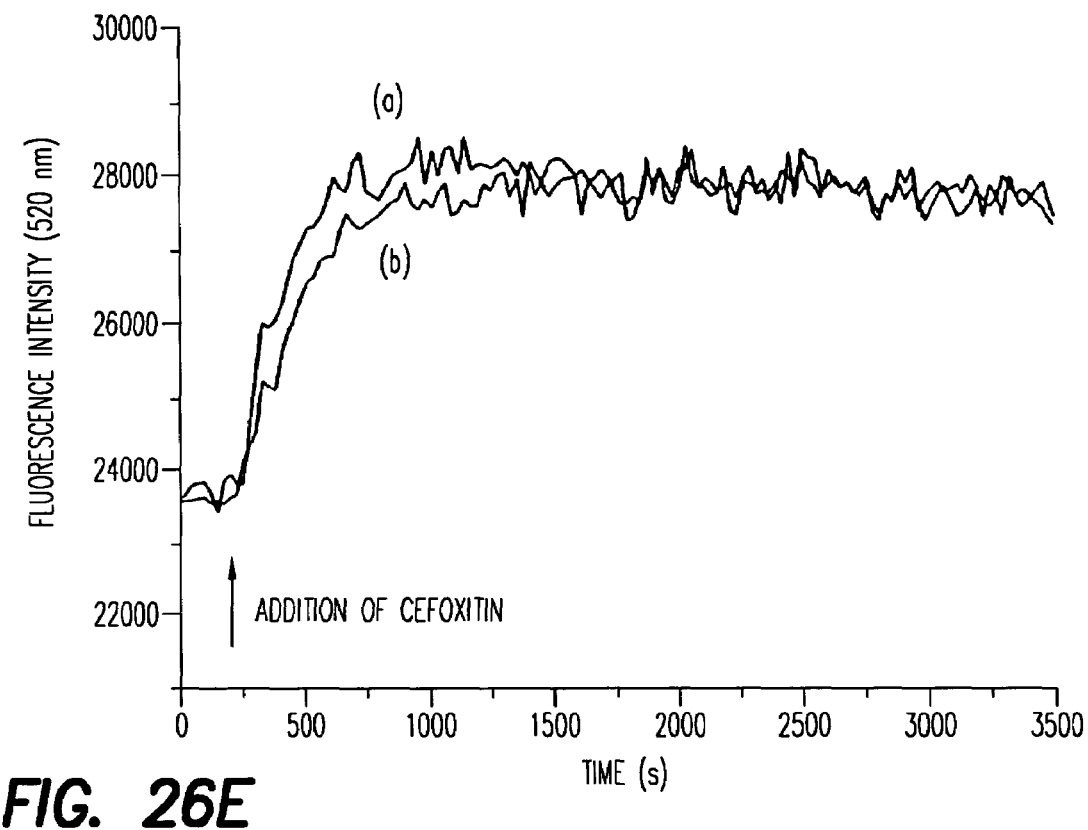
Figure 26F:
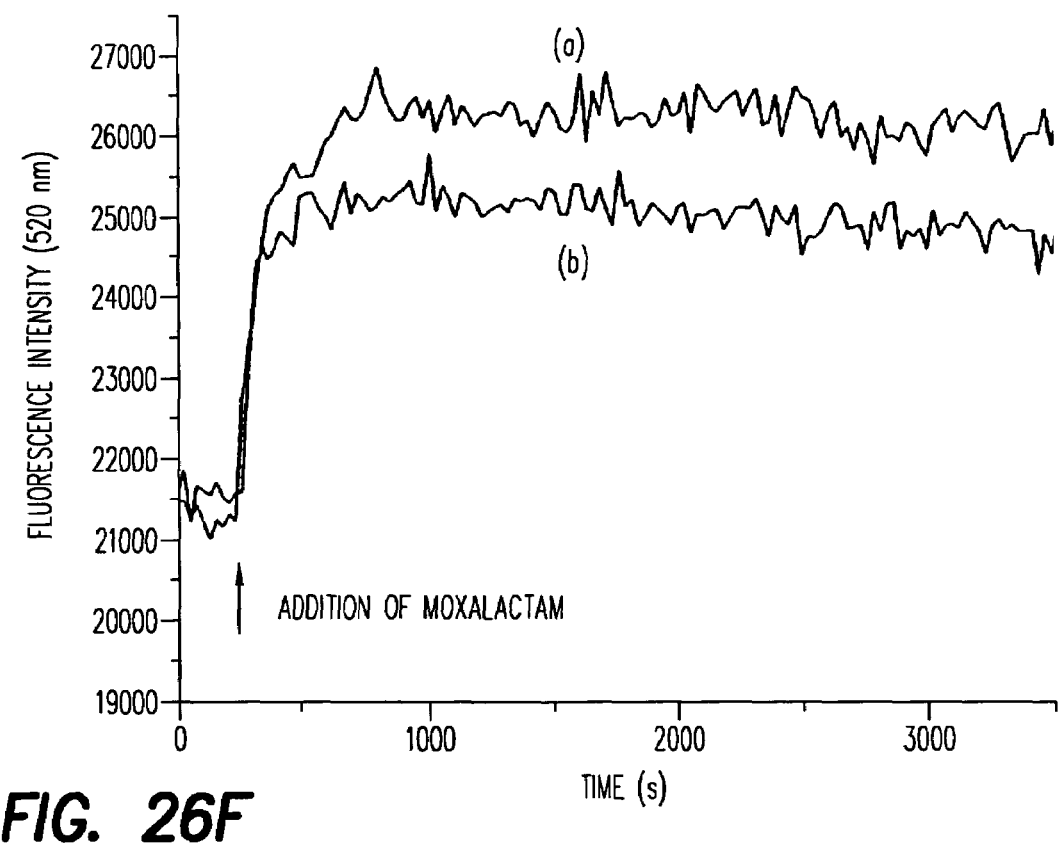

FIGS. 21 and 22 show the results from the time-resolved fluorescence measurements of the labeled enzyme ($1.2 \times 10^{-7}$ M) in untreated milk in the presence of various concentrations of penicillin G and ampicillin respectively. The results indicate that the labeled enzyme is capable of detecting penicillin G and ampicillin down to $10^{-6}$ M. Therefore, the labeled enzyme may find its application in the routine measurement of antibiotics in liquid samples (e.g. milk).

Application of the E166Cf Enzyme in Screening Bacteria for β-Lactamases against a Panel of β-Lactam Antibiotics The use of the E166Cf enzyme in screening bacterial β-lactamases against various β-lactam antibiotics was investigated. The principle of our method is that when both E166Cf and bacterial β-lactamase are incubated with 'β-lactamase-unstable' antibiotics, the fluorescence of the E166Cf enzyme will be suppressed because of the greater catalytic efficiency of the bacterial enzyme. In contrast, when bacterial β-lactamases are screened against 'β-lactamase-resistant' antibiotics, the fluorescence of the E166Cf enzyme will be enhanced because of the poor hydrolytic activity of the bacterial enzyme. Thus, any β-lactam antibiotic that causes the labeled enzyme to increase its fluorescence intensity in the presence of bacterial β-lactamases can be used in clinical treatments.

In this invention, *B. cereus* penPC β-lactamase, *B. licheniformis* penP β-lactamase, *E. coli*. TEM-1 β-lactamase and *B. cereus* β-lactamase II. were tested. *B. cereus* β-lactamase II is classified as Class B β-lactamase whereas the others are classified as Class A β-lactamase. Thus, we are interested to investigate whether the labeled enzyme can be used in screening different classes of β-lactamase against various β-lactam antibiotics.

Preparation of Bacterial β-lactamase

Bacterial β-lactamases used in the drug screening experiments were *B. cereus* penPC β-lactamase, *B. licheniformis* penP β-lactamase, *E. coli*. TEM-1 β-lactamase and *B. cereus* β-lactamase II.

The β-lactamase II, penPC β-lactamase and penP β-lactamase were expressed in *B. subtilis* 1A304 (φ105MU331). These enzymes were prepared according to the procedures described previously (Reference 7: Thomwell, S. J. East, A. K., Errington, J. An efficient expression and secretion system based on *Bacillus subtilis* phage phi 105 and its uses for the production for *B. cereus* β-lactamase I. (1993) Gene 133, 47-53) with slight modifications. A bacterial strain was streaked on an agar plate containing 5 μg/ml chloramphenicol, and the plate was incubated at 37° C. for 24 h. A single bacterial colony from the agar plate was inoculated into 100 ml of sterilized BHY medium (37 g/l brain heart infusion and 5 g/l yeast extract) which was then incubated at 37° C. with shaking at 300 rpm overnight. About 7 ml of overnight inoculum was added to a baffled conical flask containing 100 ml of sterilized BHY medium. The inoculated medium was incubated at 37° C. with shaking at 300 rpm. When the optical density of the bacterial culture at 600 nm reached 3.5 to 4.0, the bacterial culture was heated in a water bath at 51° C. for 5 min. Afterwards, the bacterial culture was incubated at 37° C. with shaking at 300 rpm for a further 6 h. The bacterial culture was then harvested and stored at −20° C.

The TEM-1 β-lactamase was expressed in *E. coli*. BL21 (DE3). Preparation of the TEM-1 β-lactamase was performed as follows. A bacterial strain was streaked on an agar plate containing 100 μg/ml ampicillin, and the plate was incubated at 37° C. for 24 h. A single bacterial colony from the plate was inoculated into 100 ml of sterilized LB broth (28 g/l) which was then incubated at 37° C. with shaking at 280 rpm overnight. After overnight incubation, the bacterial culture was harvested and stored at −20° C.

Preparation of *B. subtilis* 1A304 (φ105MU331) and *E. coli*. BL21(DE3) Cultures Both *B. subtilis* 1A304 (φ105MU331) and *E. coli*. BL21 (DE3) cultures (which produce no β-lactamase) were prepared as negative controls for drug screening experiments. Preparations of *B. subtilis* 1A304 (φ105MU331) and *E. coli*. BL21(DE3) cultures were performed as follows.

For *B. subtilis* 1A304 (φ105MU331), a bacterial strain was streaked on an agar plate containing 5 μg/ml chloramphenicol, and the plate was incubated at 37° C. for 24 h. A single bacterial colony was inoculated into 100 ml of sterilized BHY medium (37 g/l brain heart infusion and 5 g/l yeast extract) which was then incubated at 37° C. with shaking at 300 rpm overnight. After overnight incubation, the bacterial culture was harvested and stored at −20° C. For *E. coli*. BL21(DE3), a bacterial strain was streaked on an agar plate containing 100 μg/ml ampicillin, and the plate was incubated at 37° C. for 24 h. A single bacterial colony was inoculated into 100 ml of sterilized LB broth (28 g/l) which was then incubated at 37° C. with shaking at 280 rpm overnight. After overnight incubation, the bacterial culture was harvested and stored at −20° C.

Drug Screening Experiments

Fluorescence measurements of the E166Cf enzyme in the presence of bacterial cultures and β-lactam antibiotics were performed on a FLUOstar microplate reader (BMG Labtechnologies) equipped with two sample injectors. Excitation and emission filters of 485 and 520 nm respectively were used. For *B. cereus* penPC β-lactamase, *B. licheniformis* penP β-lactamase and *B. cereus* β-lactamase II, the labeled enzymes were mixed with the bacterial cultures, and the mixtures were made up to 300 μl with 50 mM phosphate buffer (pH 7.0) in a 96-well microtiter plate (Corning Costar). For the purpose of comparison, *B. subtilis* cultures, which produced no β-lactamase, were set up as negative controls. For *E. coli*. TEM-1 β-lactamase, the labeled enzymes were mixed with the bacterial cultures without dilution. *E. coli*. cultures, which produced no β-lactamase, were set up as negative controls for comparison. The antibiotics were then added to the bacterial samples by the injectors. The experimental set-up is shown in FIG. 20.

The results from the time-resolved fluorescence measurements of the labeled enzyme ($1.2 \times 10^{-7}$ M) in the presence of various bacterial cultures and β-lactam antibiotics ($1.0 \times 10^{-4}$ M) are shown in FIGS. 23 to 26. Table 2 summarizes the results obtained from the time-resolved fluorescence measurements.

TABLE 2

| | β-Lactamase | | | |
|---|---|---|---|---|
| | B. cereus β-lactamase II | B. cereus penPC | B. licheniformis penP | E. coli TEM-1 |
| Penicillin G | − | − | − | − |
| Penicillin V | − | − | − | − |
| Ampicillin | − | − | − | − |
| Cefuroxime | − | + | − | + |
| Cefoxitin | + | + | + | + |
| Moxalactam | + | + | + | + |

− Decline in fluorescence signal (presence of beta-lactam hydrolysis)
+ No decline in fluorescence signal (absence of beta-lactam hydrolysis)

The results indicate that cefoxitin and moxalactam are resistant to the hydrolytic activities of the bacterial β-lactamases, and therefore can be used in the clinical treatment if patients are infected with bacteria which produce such β-lactamases.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

The invention claimed is:

1. A method for detecting β-lactam antibiotics or β-lactamase inhibitors in a sample, comprising the steps of:
   (1) providing a modified β-lactamase for binding with said β-lactam antibiotics or β-lactamase inhibitors, wherein the modified β-lactamase is a wild-type β-lactamase having a residue at a position that corresponds to a position in the amino acid sequence of the *Bacillus cereus* β-lactamase I selected from the group consisting of Ser70, Lys73, Asp104, Ser130, Asn163, Arg164, Phe165, Thr167, Glu168, Leu169, Asn170, Glu171, Ala172, Ile173, Pro174, Gly175, Asp176, Ile177, Arg178, and Lys234 replaced by an amino acid selected from the group consisting of an amino acid containing a free thiol group, an amino acid containing a free carboxylic acid group, and an amino acid containing a free amine group, and the replacing amino acid is covalently bonded to a fluorescent indicator for generating a change of fluorescence upon binding β-lactam antibiotics or β-lactamase inhibitors,
   (2) exposing the sample to said modified β-lactamase comprising a fluorescent indicator molecule, and
   (3) comparing the fluorescence emitted by the modified β-lactamase bound with said β-lactam antibiotics or β-lactamase inhibitors, with the fluorescence emitted by the β-lactamase from a control sample having no β-lactam antibiotics or β-lactamase inhibitor,
   whereby the presence of β-lactam antibiotics or β-lactamase inhibitors in a sample is detected.

2. The method as claimed in claim 1, wherein the replacing amino acid is cysteine.

3. The method as claimed in claim 1, wherein the indicator molecule is a fluorophore.

* * * * *